US012570611B2

(12) United States Patent
Lopchuk et al.

(10) Patent No.: US 12,570,611 B2
(45) Date of Patent: Mar. 10, 2026

(54) PROCESSES AND COMPOUNDS FOR THE DECARBOXYLATIVE AMINATION OF REDOX-ACTIVE ESTERS WITH DIAZIRINES

(71) Applicant: H. LEE MOFFITT CANCER CENTER AND RESEARCH INSTITUTE, INC., Tampa, FL (US)

(72) Inventors: Justin M. Lopchuk, Tampa, FL (US); Preeti P. Chandrachud, Tampa, FL (US)

(73) Assignee: H. LEE MOFFITT CANCER CENTER AND RESEARCH INSTITUTE, INC., Tampa, FL (US)

( * ) Notice: Subject to any disclaimer, the term of this patent is extended or adjusted under 35 U.S.C. 154(b) by 805 days.

(21) Appl. No.: 17/617,973

(22) PCT Filed: Jun. 15, 2020

(86) PCT No.: PCT/US2020/037742
§ 371 (c)(1),
(2) Date: Dec. 10, 2021

(87) PCT Pub. No.: WO2020/252457
PCT Pub. Date: Dec. 17, 2020

(65) Prior Publication Data

US 2022/0274930 A1 Sep. 1, 2022

Related U.S. Application Data

(60) Provisional application No. 62/861,586, filed on Jun. 14, 2019.

(51) Int. Cl.
*C07D 229/02* (2006.01)
*C07D 211/96* (2006.01)
*C07D 401/04* (2006.01)

(52) U.S. Cl.
CPC .......... *C07D 229/02* (2013.01); *C07D 211/96* (2013.01); *C07D 401/04* (2013.01)

(58) Field of Classification Search
CPC .................................................... C07D 229/02
See application file for complete search history.

(56) References Cited

U.S. PATENT DOCUMENTS

2014/0303333 A1 10/2014 Shaver et al.

FOREIGN PATENT DOCUMENTS

WO 1997000265 A1 1/1997

OTHER PUBLICATIONS

Database Registry Chemical Abstracts Service, Columbus, Ohio, Accession No. RN 1191250-80-2, Entered STN: Nov. 5, 2009.*
Vitaku, Edon, David T. Smith, and Jon T. Njardarson. "Analysis of the structural diversity, substitution patterns, and frequency of nitrogen heterocycles among US FDA approved pharmaceuticals: miniperspective." Journal of medicinal chemistry 57.24 (2014): 10257-10274.
Ilardi, Elizabeth A., Edon Vitaku, and Jon T. Njardarson. "An in-pharm-ative educational poster anthology highlighting the therapeutic agents that chronicle our medicinal history." Journal of Chemical Education 90.10 (2013): 1403-1405.
Ilardi, Elizabeth A., Edon Vitaku, and Jon T. Njardarson. "Data-mining for sulfur and fluorine: An evaluation of pharmaceuticals to reveal opportunities for drug design and discovery: Miniperspective." Journal of medicinal chemistry 57.7 (2014): 2832-2842.
Gale, David M., William J. Middleton, and Carl G. Krespan. "Perfluorodiazo compounds." Journal of the American Chemical Society 88.15 (1966): 3617-3623.
Barton, Derek HR, Joseph C. Jaszberenyi, and Emmanouil A. Theodorakis. "Nitrogen transfer to carbon radicals." Journal of the American Chemical Society 114.14 (1992): 5904-5905.
International Preliminary Report on Patentability issued for Application No. PCT/US2020/037742, dated Dec. 23, 2021.
Pubchem, Substance Record for SID 273896682. Dec. 18, 2015. pubchem.ncbi.nlm.nih.gov/substance/273896682.
International Search Report and Written Opinion in PCT/US2020/037742. Mailed Sep. 14, 2020. 9 pages.

* cited by examiner

*Primary Examiner* — Yong S. Chong
(74) *Attorney, Agent, or Firm* — Meunier Carlin & Curfinan LLC

(57) ABSTRACT

The invention described herein relates generally to processes for the synthesis of amine-containing organic compounds. More specifically, described herein relates to processes for the decarboxylative amination of redox-active esters with diazirines and the products formed thereof. Compounds for use in the above processes are also described.

1 Claim, 4 Drawing Sheets

1
dioxiranes
3
-aziridiniums
2
oxaziridines
4
diazirines or
4
5

Krespan:

6
7
(4-5 equiv.)
8 (40%)
9 (19%)

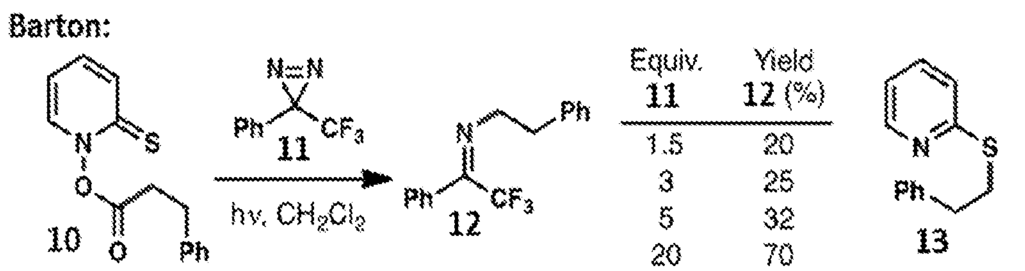

| Equiv. 11 | Yield 12 (%) |
|---|---|
| 1.5 | 20 |
| 3 | 25 |
| 5 | 32 |
| 20 | 70 |

FIG. 2B

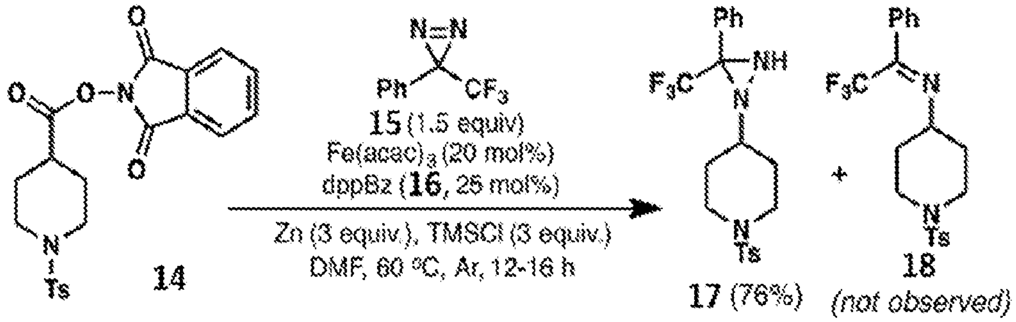

| entry | deviation from above | yield (%) | entry | deviation from above | yield (%) |
|---|---|---|---|---|---|
| 1 | $NiCl_2$•glyme/19 | 0 | 7 | 1.5 equiv. Zn/TMSCl | 46 |
| 2 | $NiCl_2$•$6H_2O$/19 | 50 | 8 | without TMSCl | 22 |
| 3 | dppe (20) | 33 | 9 | TCNHPI ester | 10 |
| 4 | dppp (21) | 41 | 10 | 23 instead of 15 | 0 |
| 5 | dppb (22) | 66 | 11 | 24 instead of 15 | 0 |
| 6 | $FeCl_3$•$6H_2O$/16 | 66 | 12 | no precautions | 76 |

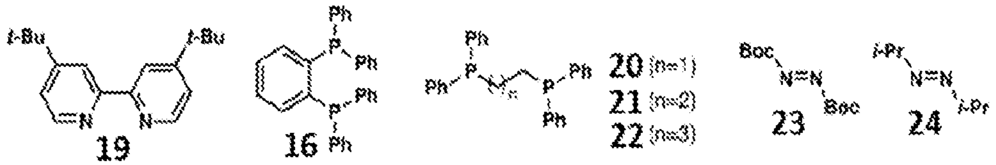

FIG. 2C

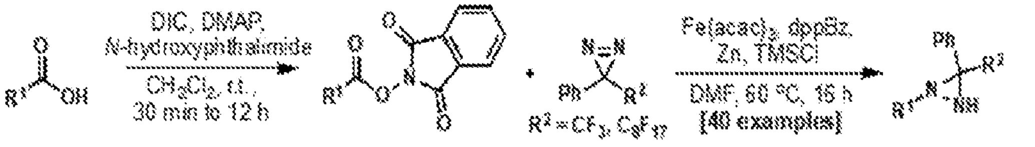

- Primary, secondary and tertiary acids
- Broad functional group tolerance
- Gram-scale and one-pot operations
- Late-stage amination of natural products and pharmaceutical compounds

FIG. 3

PROCESSES AND COMPOUNDS FOR THE DECARBOXYLATIVE AMINATION OF REDOX-ACTIVE ESTERS WITH DIAZIRINES

CROSS-REFERENCE TO RELATED APPLICATIONS

The present disclosure is the national phase under 35 U.S.C 371 of PCT/US2020/037742 filed on Jun. 15, 2020, which claims the benefit of priority to U.S. Provisional Application No. 62/861,586, filed Jun. 14, 2019, both of which are incorporated herein by reference in their entireties.

STATEMENT REGARDING FEDERALLY SPONSORED RESEARCH OR DEVELOPMENT

This disclosure was made with Government Support under Grant No. CHE-1903144 awarded by the National Science Foundation. The Government has certain rights to this disclosure.

FIELD

The subject matter disclosed herein relates generally to processes for the synthesis of amine-containing organic compounds. More specifically, the subject matter disclosed herein relates to processes for the decarboxylative amination of redox-active esters with diazirines and the products formed thereof. Compounds for use in the above processes are also described.

BACKGROUND

Amines, hydrazines, and other nitrogen-containing functional groups are ubiquitous in industrial processes, pharmaceuticals, natural products, materials, and dyes. As of 2014, 84% of all small molecule pharmaceuticals contained at least one nitrogen, with an average approximately 2.3 nitrogen atoms per drug (see J. Med. Chem., 2014, 57, 10257-10274). When considering only oncology drugs, roughly 76% contain nitrogen (see J. Chem. Ed., 2013, 90, 1403-1405). In contrast, sulfur and nitrogen, two atoms that are regularly used in medicinal chemistry, appear in just 23% and 13% of pharmaceuticals, respectively (see J. Med. Chem. 2014, 57, 2832-2842). Nearly all therapeutic areas are dependent upon the development of nitrogen-containing compounds, including the treatment of cognitive disorders, cardiac health, pain relief, and oncology. Thus, new methods are needed for the synthesis of amine-containing organic compounds as well as new reagent compounds for use in those methods. The processes and compounds disclosed herein address these and other needs.

SUMMARY

In accordance with the purposes of the disclosed materials and methods, as embodied and broadly described herein, the disclosed subject matter, in one aspect, relates to processes of making compounds in addition to specific compounds for use in those processes. More specifically, the subject matter disclosed herein relates to a process for the decarboxylative amination of redox-active esters with diazirines and the products formed thereof.

Additional advantages will be set forth in part in the description that follows, and in part will be obvious from the description, or may be learned by practice of the aspects described below. The advantages described below will be realized and attained by means of the elements and combinations particularly pointed out in the appended claims. It is to be understood that both the foregoing general description and the following detailed description are exemplary and explanatory only and are not restrictive.

DESCRIPTION OF THE FIGURES

FIG. 1A depicts heteroatom transfer via tree-membered heterocyclic reagents. FIG. 1B depicts the conceptual use of diaziridines as a diversity-enabling disconnection in the synthesis of amines, hydrazines, and nitrogen-containing heterocycles.

FIGS. 2A, 2B, and 2C depict prior reactions of diazirines and the development of diazirine-based decarboxylative amination. FIG. 2A depicts Krespan's reaction of diazirine with cyclohexane.

FIG. 2B depicts Barton's reaction of diazirine with thiohydroxamate ester. FIG. 2C shows the optimization of the reaction of diazirine with redox-active esters. All yields refer to isolated compounds.

FIG. 3 shows the generic conditions for decarboxylative amination of redox-active esters with diazirines described herein. Reaction conditions: redox-active ester (1.0 equiv.), diazirine (1.5 equiv. unless otherwise noted), $Fe(acac)_3$ (20 mol %), dppBz (25 mol %), zin (3 equiv.), TMSCl (3 equiv.), DMF, 60° C., 16 h.

FIG. 4A depicts the selective conversion of diaziridines to amines or hydrazines with recovery of ketone. FIG. 4B depicts the one-pot synthesis of amines from diazirines and redox-active esters. FIG. 4C depicts the one-pot and/or telescoped conversion of diaziridine to various medicinally-relevant heterocycles. Isolated yields are reported.

FIG. 2A depicts the chromatography-free F-SPE synthesis and purification of diaziridine products formed by the processes described herein. FIG. 2B depicts the chromatography-free F-SPE synthesis and purification of an amine produced from the diaziridines described herein with concomitant recovery of ketone.

Like reference symbols in the various drawings indicate like elements.

DETAILED DESCRIPTION

Figure 1A:
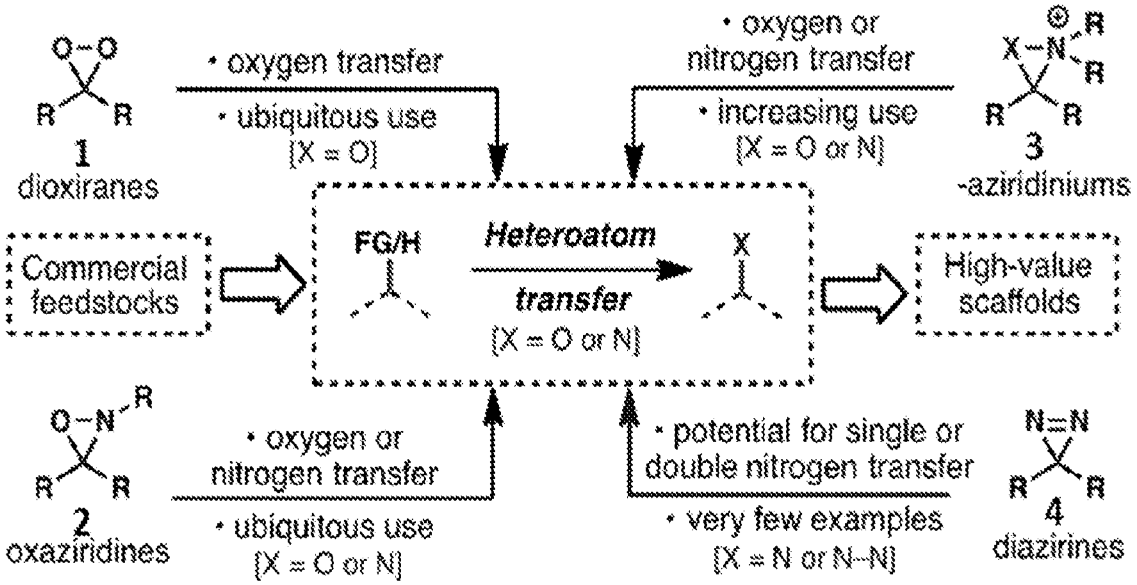
FIGS. 1A and 1B depict synthetic methods for strain-release driven heteroatom transfer.

The materials, compounds, compositions, and methods described herein may be understood more readily by reference to the following detailed description of specific aspects of the disclosed subject matter, the Figures, and the Examples included therein.

Before the present materials, compounds, compositions, and methods are disclosed and described, it is to be understood that the aspects described below are not limited to specific synthetic methods or specific reagents, as such may, of course, vary. It is also to be understood that the terminology used herein is for the purpose of describing particular aspects only and is not intended to be limiting.

Also, throughout this specification, various publications are referenced. The disclosures of these publications in their entireties are hereby incorporated by reference into this application in order to more fully describe the state of the art to which the disclosed matter pertains. The references disclosed are also individually and specifically incorporated by reference herein for the material contained in them that is discussed in the sentence in which the reference is relied upon.

General Definitions

In this specification and in the claims that follow, reference will be made to a number of terms, which shall be defined to have the following meanings:

Throughout the specification and claims the word "comprise" and other forms of the word, such as "comprising" and "comprises," means including but not limited to, and is not intended to exclude, for example, other additives, components, integers, or steps.

As used in the description and the appended claims, the singular forms "a," "an," and "the" include plural referents unless the context clearly dictates otherwise. Thus, for example, reference to "a composition" includes mixtures of two or more such compositions, reference to "an inhibitor" includes mixtures of two or more such inhibitors, reference to "the kinase" includes mixtures of two or more such kinase, and the like.

"Optional" or "optionally" means that the subsequently described event or circumstance can or cannot occur, and that the description includes instances where the event or circumstance occurs and instances where it does not.

Notwithstanding that the numerical ranges and parameters setting forth the broad scope of the disclosure are approximations, the numerical values set forth in the specific examples are reported as precisely as possible. Any numerical value, however, inherently contain certain errors necessarily resulting from the standard deviation found in their respective testing measurements. Furthermore, when numerical ranges of varying scope are set forth herein, it is contemplated that any combination of these values inclusive of the recited values may be used. Further, ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint. Unless stated otherwise, the term "about" means within 5% (e.g., within 2% or 1%) of the particular value modified by the term "about."

It is understood that throughout this specification the identifiers "first" and "second" are used solely to aid in distinguishing the various components and steps of the disclosed subject matter. The identifiers "first" and "second" are not intended to imply any particular order, amount, preference, or importance to the components or steps modified by these terms.

Chemical Definitions

As used herein, the term "composition" is intended to encompass a product comprising the specified ingredients in the specified amounts, as well as any product which results, directly or indirectly, from combination of the specified ingredients in the specified amounts.

References in the specification and concluding claims to parts by weight of a particular element or component in a composition denotes the weight relationship between the element or component and any other elements or components in the composition or article for which a part by weight is expressed. Thus, in a mixture containing 2 parts by weight of component X and 5 parts by weight component Y, X and Y are present at a weight ratio of 2:5, and are present in such ratio regardless of whether additional components are contained in the mixture.

A weight percent (wt. %) of a component, unless specifically stated to the contrary, is based on the total weight of the formulation or composition in which the component is included.

As used herein, the term "substituted" is contemplated to include all permissible substituents of organic compounds. In a broad aspect, the permissible substituents include acyclic and cyclic, branched and unbranched, carbocyclic and heterocyclic, and aromatic and nonaromatic substituents of organic compounds. Illustrative substituents include, for example, those described below. The permissible substituents can be one or more and the same or different for appropriate organic compounds. For purposes of this disclosure, the heteroatoms, such as nitrogen, can have hydrogen substituents and/or any permissible substituents of organic compounds described herein which satisfy the valencies of the heteroatoms. This disclosure is not intended to be limited in any manner by the permissible substituents of organic compounds. Also, the terms "substitution" or "substituted with" include the implicit proviso that such substitution is in accordance with permitted valence of the substituted atom and the substituent, and that the substitution results in a stable compound, e.g., a compound that does not spontaneously undergo transformation such as by rearrangement, cyclization, elimination, etc.

The term "aliphatic" as used herein refers to a non-aromatic hydrocarbon group and includes branched and unbranched, alkyl, alkenyl, or alkynyl groups.

The term "alkyl" as used herein is a branched or unbranched saturated hydrocarbon group of 1 to 24 carbon atoms, such as methyl, ethyl, n-propyl, isopropyl, n-butyl, isobutyl, t-butyl, pentyl, hexyl, heptyl, octyl, nonyl, decyl, dodecyl, tetradecyl, hexadecyl, eicosyl, tetracosyl, and the like. The alkyl group can also be substituted or unsubstituted. The alkyl group can be substituted with one or more groups including, but not limited to, alkyl, halogenated alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol, as described below.

As described herein, "perfluoroalkyl" is an alkyl group as described herein where each hydrogen substituent on the group has been substituted with a fluorine atom. In some embodiments, perfluoroalkyl may be selected from $—CF_3$, $—C_2F_5$, $—C_3F_7$, $—C_4F_9$, $—C_5F_{11}$, $—C_6F_{13}$, $—C_7F_{15}$, $—C_8F_{17}$, $—C_9F_{19}$, $—C_{10}F_{21}$, $—C_{11}F_{23}$, $—C_{12}F_{25}$, $—C_{13}F_{27}$, and $—C_{14}F_{29}$. Representative but non-limiting examples of "perfluoroalkyl" groups include trifluoromethyl, pentafluoroethyl, or heptadecafluorooctyl.

The symbols $A^n$ is used herein as merely a generic substituent in the definitions below.

The term "alkoxy" as used herein is an alkyl group bound through a single, terminal ether linkage; that is, an "alkoxy" group can be defined as $—OA^1$ where $A^1$ is alkyl as defined above.

The term "alkenyl" as used herein is a hydrocarbon group of from 2 to 24 carbon atoms with a structural formula containing at least one carbon-carbon double bond. Asymmetric structures such as $(A^1A^2)C{=}C(A^3A^4)$ are intended to include both the E and Z isomers. This may be presumed in structural formulae herein wherein an asymmetric alkene is present, or it may be explicitly indicated by the bond symbol C═C. The alkenyl group can be substituted with one or more groups including, but not limited to, alkyl, halogenated alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol, as described below.

The term "alkynyl" as used herein is a hydrocarbon group of 2 to 24 carbon atoms with a structural formula containing at least one carbon-carbon triple bond. The alkynyl group can be substituted with one or more groups including, but not limited to, alkyl, halogenated alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol, as described below.

The term "aryl" as used herein is a group that contains any carbon-based aromatic group including, but not limited to, benzene, naphthalene, phenyl, biphenyl, phenoxybenzene, and the like. The term "heteroaryl" is defined as a group that contains an aromatic group that has at least one heteroatom incorporated within the ring of the aromatic group. Examples of heteroatoms include, but are not limited to, nitrogen, oxygen, sulfur, and phosphorus. The term "non-heteroaryl," which is included in the term "aryl," defines a group that contains an aromatic group that does not contain a heteroatom. The aryl and heteroaryl group can be substituted or unsubstituted. The aryl and heteroaryl group can be substituted with one or more groups including, but not limited to, alkyl, halogenated alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol as described herein. The term "biaryl" is a specific type of aryl group and is included in the definition of aryl. Biaryl refers to two aryl groups that are bound together via a fused ring structure, as in naphthalene, or are attached via one or more carbon-carbon bonds, as in biphenyl.

The term "cycloalkyl" as used herein is a non-aromatic carbon-based ring composed of at least three carbon atoms. Examples of cycloalkyl groups include, but are not limited to, cyclopropyl, cyclobutyl, cyclopentyl, cyclohexyl, etc. The term "heterocycloalkyl" is a cycloalkyl group as defined above where at least one of the carbon atoms of the ring is substituted with a heteroatom such as, but not limited to, nitrogen, oxygen, sulfur, or phosphorus. The cycloalkyl group and heterocycloalkyl group can be substituted or unsubstituted. The cycloalkyl group and heterocycloalkyl group can be substituted with one or more groups including, but not limited to, alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol as described herein.

The term "cycloalkenyl" as used herein is a non-aromatic carbon-based ring composed of at least three carbon atoms and containing at least one double bound, i.e., C═C. Examples of cycloalkenyl groups include, but are not limited to, cyclopropenyl, cyclobutenyl, cyclopentenyl, cyclopentadienyl, cyclohexenyl, cyclohexadienyl, and the like. The term "heterocycloalkenyl" is a type of cycloalkenyl group as defined above where at least one of the carbon atoms of the ring is substituted with a heteroatom such as, but not limited to, nitrogen, oxygen, sulfur, or phosphorus. The cycloalkenyl group and heterocycloalkenyl group can be substituted or unsubstituted. The cycloalkenyl group and heterocycloalkenyl group can be substituted with one or more groups including, but not limited to, alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol as described herein.

The term "cyclic group" is used herein to refer to either aryl groups, non-aryl groups (i.e., cycloalkyl, heterocycloalkyl, cycloalkenyl, and heterocycloalkenyl groups), or both. Cyclic groups have one or more ring systems that can be substituted or unsubstituted. A cyclic group can contain one or more aryl groups, one or more non-aryl groups, or one or more aryl groups and one or more non-aryl groups.

The term "aldehyde" as used herein is represented by the formula —C(O)H. Throughout this specification "C(O)" is a short hand notation for C═O.

The terms "amine" or "amino" as used herein are represented by the formula $NA^1A^2A^3$, where $A^1$, $A^2$, and $A^3$ can be, independently, hydrogen, an alkyl, halogenated alkyl, alkenyl, alkynyl, aryl, heteroaryl, cycloalkyl, cycloalkenyl, heterocycloalkyl, or heterocycloalkenyl group described above.

The term "carboxylic acid" as used herein is represented by the formula —C(O)OH. A "carboxylate" as used herein is represented by the formula $—C(O)O^-$.

The term "ester" as used herein is represented by the formula $—OC(O)A^1$ or $—C(O)OA^1$, where $A^1$ can be an alkyl, halogenated alkyl, alkenyl, alkynyl, aryl, heteroaryl, cycloalkyl, cycloalkenyl, heterocycloalkyl, or heterocycloalkenyl group described above.

The term "ether" as used herein is represented by the formula $A^1OA^2$, where $A^1$ and $A^2$ can be, independently, an alkyl, halogenated alkyl, alkenyl, alkynyl, aryl, heteroaryl, cycloalkyl, cycloalkenyl, heterocycloalkyl, or heterocycloalkenyl group described above.

The term "ketone" as used herein is represented by the formula $A^1C(O)A^2$, where $A^1$ and $A^2$ can be, independently, an alkyl, halogenated alkyl, alkenyl, alkynyl, aryl, heteroaryl, cycloalkyl, cycloalkenyl, heterocycloalkyl, or heterocycloalkenyl group described above.

The term "halide" as used herein refers to the halogens fluorine, chlorine, bromine, and iodine.

The term "hydroxyl" as used herein is represented by the formula —OH.

The term "nitro" as used herein is represented by the formula $—NO_2$.

The term "cyano" as used herein is represented by the formula —CN

The term "azido" as used herein is represted by the formula $—N_3$.

The term "sulfonyl" is used herein to refer to the sulfo-oxo group represented by the formula $—S(O)_2A^1$, where $A^1$ can be hydrogen, an alkyl, halogenated alkyl, alkenyl, alkynyl, aryl, heteroaryl, cycloalkyl, cycloalkenyl, heterocycloalkyl, or heterocycloalkenyl group described above.

The term "sulfonylamino" or "sulfonamide" as used herein is represented by the formula $—S(O)_2NH_2$.

The term "thiol" as used herein is represented by the formula —SH.

It is to be understood that the compounds provided herein may contain chiral centers. Such chiral centers may be of either the (R-) or (S-) configuration. The compounds provided herein may either be enantiomerically pure, or be diastereomeric or enantiomeric mixtures. It is to be understood that the chiral centers of the compounds provided herein may undergo epimerization in vivo. As such, one of skill in the art will recognize that administration of a compound in its (R-) form is equivalent, for compounds that undergo epimerization in vivo, to administration of the compound in its (S-) form.

As used herein, substantially pure means sufficiently homogeneous to appear free of readily detectable impurities as determined by standard methods of analysis, such as thin layer chromatography (TLC), nuclear magnetic resonance (NMR), gel electrophoresis, high performance liquid chromatography (HPLC) and mass spectrometry (MS), gas-chromatography mass spectrometry (GC-MS), and similar, used by those of skill in the art to assess such purity, or sufficiently pure such that further purification would not detectably alter the physical and chemical properties, such as enzymatic and biological activities, of the substance. Both traditional and modern methods for purification of the compounds to produce substantially chemically pure compounds are known to those of skill in the art. A substantially chemically pure compound may, however, be a mixture of stereoisomers.

Unless stated to the contrary, a formula with chemical bonds shown only as solid lines and not as wedges or dashed lines contemplates each possible isomer, e.g., each enantiomer, diastereomer, and meso compound, and a mixture of isomers, such as a racemic or scalemic mixture.

Reference will now be made in details to specific aspects of the disclosed materials, compounds, compositions, articles, and methods, examples of which are illustrated in the accompanying Examples and Figures.

Processes for the Decarboxylative Amination of Redox-Active Esters with Diazirines Disclosed are methods for the synthesis of nitrogen-containing organic compounds by the reaction of a redox-active ester with a diazirine compound. As used herein, a "redox active ester" is a compound containing an ester functional group that is able to accept an electron in a single electron transfer (SET) fashion. As used herein, a "diazirine" is a functional group having the structure

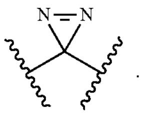 [SMILES: *C1(*)N=N1]

Thus, a process is provided for the synthesis of a compound of Formula III:

(III)

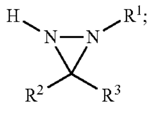

or a salt or other suitable derivative thereof, wherein:

$R^1$ is selected from alkyl, alkenyl, alkynyl, cycloalkyl, cycloalkenyl, heterocycloalkyl, heterocycloalkenyl, aryl, and heteroaryl, wherein $R^1$ may be optionally substituted one or groups selected from alkyl, halogenated alkyl, alkoxy, alkenyl, alkynyl, aryl, heteroaryl, aldehyde, amino, carboxylic acid, ester, ether, halide, hydroxy, ketone, nitro, cyano, silyl, sulfo-oxo, sulfonyl, sulfone, sulfoxide, sulfonamide, thiol, and combinations thereof;

$R^2$ is selected from alkyl, cycloalkyl, heterocycloalkyl, aryl, or heteroaryl, wherein $R^2$ may be optionally substituted with one or more groups selected form alkyl, halogenated alkyl, alkoxy, alkenyl, alkynyl, aryl, heteroaryl, aldehyde, amino, carboxylic acid, ester, ether, halide, hydroxy, ketone, nitro, cyano, silyl, sulfo-oxo, sulfonyl, sulfone, sulfoxide, sulfonamide, thiol, and combinations thereof;

$R^3$ is selected from alkyl or perfluoroalkyl, wherein if $R^3$ except for perfluoroalkyl can be optionally substituted with one or more groups selected form alkyl, halogenated alkyl, alkoxy, alkenyl, alkynyl, aryl, heteroaryl, aldehyde, amino, carboxylic acid, ester, ester, halide, hydroxy, hetone, nitro, silyl, sulfo-oxo, sulfonyl, sulfone, sulfoxide, thiol, and combinations thereof;

or $R^2$ and $R^3$ may be brought together with the carbon to which they are attached to form a cycloalkyl or heterocycloalkyl ring optionally substituted with one or more groups selected from alkyl, halogenated alkyl, alkoxy, alkenyl, alkynyl, aryl, heteroaryl, aldehyde, amino, carboxylic acid, ester, ether, halide, hydroxy, ketone, nitro, cyano, silyl, sulfo-oxo, sulfonyl, sulfone, sulfoxide, sulfonamide, thiol, and combinations thereof;

the process comprising:

providing a compound of Formula I:

(I)

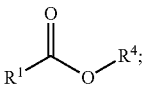

or a salt or other suitable derivative thereof, wherein:

$R^4$ is

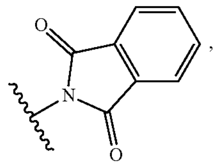 [SMILES: *N1C(=O)c2ccccc2C1=O]

wherein $R^4$ may be optionally substituted as allowed by valence with one or more groups selected from alkyl, halogenated alkyl, alkoxy, alkenyl, alkynyl, aryl, heteroaryl, aldehyde, amino, carboxylic acid, ester, ether, halide, hydroxy, ketone, nitro, cyano, silyl, sulfo-oxo, sulfonyl, sulfone, sulfoxide, sulfonamide, thiol, and combinations thereof;

providing a compound of Formula II:

(II)

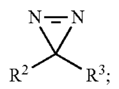

or a salt of other suitable derivative thereof, wherein all variables are as defined herein;

and contacting and reacting the compound of Formula I with the compound of Formula II in the presence of an iron catalyst, a phosphine ligand, and a reductant at a temperature from about 70° C. to about 90° C. to provide the compound of Formula III.

In some embodiments, $R^2$ is aryl. In some embodiments, $R^2$ is phenyl.

In some embodiments, $R^3$ is perfluoroalkyl. In some embodiments, $R^3$ is $C_4$-$C_{14}$ perfluoroalkyl. In some embodiments, $R^3$ is $C_4F_9$. In some embodiments, $R^3$ is $C_5F_{11}$. In some embodiments, $R^3$ is $C_6F_{13}$. In some embodiments, $R^3$ is $C_7F_{15}$. In some embodiments, $R^3$ is $C_8F_{17}$. In some embodiments, $R^3$ is $C_9F_{19}$. In some embodiments, $R^3$ is $C_{10}F_{21}$. In some embodiments, $R^3$ is $C_{11}F_{23}$. In some embodiments, $R^3$ is $C_{12}F_{25}$. In some embodiments, $R^3$ is $C_{13}F_{27}$. In some embodiments, $R^3$ is $C_{14}F_{29}$. In some embodiments, $R^3$ is trifluoromethyl.

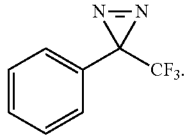 [SMILES: FC(F)(F)C1(c2ccccc2)N=N1]

In some embodiments, the compound of Formula II is

In some embodiments, the compound of Formula II is:

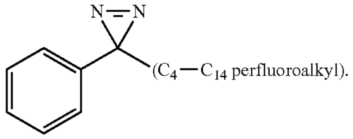

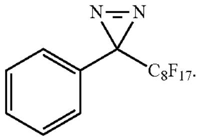

In some embodiments, the compound of Formula II is

In some embodiments, $R^2$ and $R^3$ are brought together with the carbon to which they are attached to form a heterocycloalkyl group. In some embodiments, the compound of Formula II is:

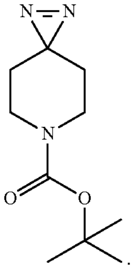

In some embodiments, the compound of Formula II is provided in about 1.5 molar equivalents as compared to the moles provided of the compound of Formula I.

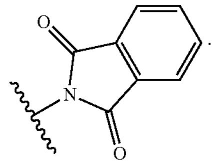 [SMILES: *N1C(=O)c2ccccc2C1=O]

In some embodiments, $R^4$ is

In some embodiments, R4 is substituted with 1, 2, 3, or 4 halogen groups, for example 1, 2, 3, or 4 chloro groups. In some embodiments, $R^4$ is

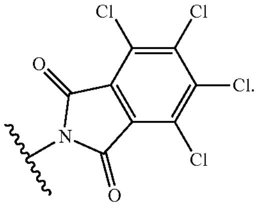 [SMILES: *N1C(=O)c2c(Cl)c(Cl)c(Cl)c(Cl)c2C1=O]

In some embodiments, the iron catalyst is $Fe(acac)_3$. In other embodiments, the iron catalyst is $FeCl_3$. In some embodiments, the iron catalyst is provided at about 20 mol % as compared to the moles provided of the compound of Formula I. In some embodiments, $Fe(acac)_3$ is provided at about 20 mol % as compared to the moles provided of the compound of Formula I.

In some embodiments, the phosphine ligand is 1,2-bis(diphenylphosphino)benzene, i.e. dppBz. In other embodiments, the phosphine ligand is 1,2-bis(diphenylphosphino)ethane, i.e. dppe. In other embodiments, the phosphine ligand is 1,3-bis(diphenylphosphino)propane, i.e. dppp. In other embodiments, the phosphine ligand is triphenylphosphine. In other embodiments, the phosphine ligand is 4,5-bis(diphenylphosphine)-9,9-dimethylxanthene, i.e. Xantphos. In some embodiments, the phosphine ligand is provided at about 25 mol % as compared to the moles provided of the compound of Formula I. In some embodiments, dppBz is provided at about 25 mol % as compared to the moles provided of the compound of Formula I.

In some embodiments, the reductant is metallic zinc. In some embodiments, the reductant is provided in about 3 molar equivalents as compared to the molar equivalents provided of the compound of Formula I. In some embodiments, metallic zinc is provided in about 3 molar equivalents as compared to the molar equivalents provided of the compound of Formula I. In some embodiments, the reductant further comprises trimethylsilyl chloride. Metallic zinc as used in the present invention may be provided as a powder, as granules, as a foil, or as wire. In some embodiments, the reductant is metallic zinc powder. In some embodiments, trimethylsilylchloride is provided in about 3 molar equivalents as compared to the molar equivalents provided of the compound of Formula I.

In some embodiments, the iron catalyst is $Fe(acac)_3$, the phosphine ligand is dppBz, the reductant is metallic zinc and trimethylsilylchloride.

In some embodiments, the process further comprises a solvent. In some embodiments, the solvent is a polar aprotic solvent. In one embodiment, the solvent is dimethylformamide In another embodiment, the solvent is dimethylacetamide. In another embodiment, the solvent is dimethylsulfoxide.

In some embodiments, the temperature of the contacting and reacting step of the above process is from about 75° C.

to about 85° C. In some embodiments, the temperature of the contacting and reacting step is about 80° C.
Representative examples of compound prepared by the above process are provided in Table 1.
TABLE 1
Compounds of Formula III Prepared by Above Process
| Entry | Compound | Yield (%) |
|---|---|---|
| A | 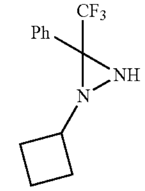 [SMILES: FC(F)(F)C1(c2ccccc2)NN1C1CCC1] | 50 |
| B | 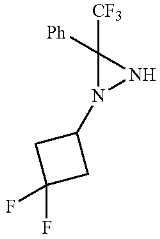 | 50 |
| C | 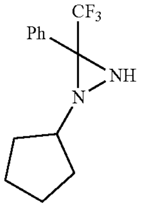 [SMILES: FC(F)(F)C1(c2ccccc2)NN1C1CCCC1] | 67 |
| D | 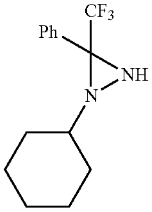 [SMILES: FC(F)(F)C1(c2ccccc2)NN1C1CCCCC1] | 76 |
| E | 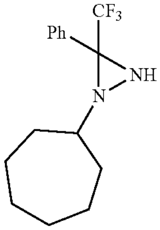 [SMILES: FC(F)(F)C1(c2ccccc2)NN1C1CCCCCC1] | 83 |
| F | 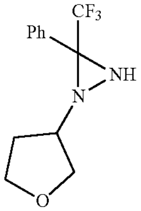 [SMILES: FC(F)(F)C1(c2ccccc2)NN1C1CCOC1] | 59 |

TABLE 1-continued
| Compounds of Formula III Prepared by Above Process | | |
|---|---|---|
| Entry | Compound | Yield (%) |
| G | 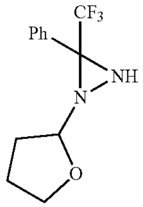 [SMILES: FC(F)(F)C1(c2ccccc2)NN1C1CCCO1] | 38 |
| H | 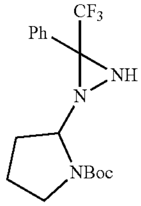 [SMILES: CC(C)(C)OC(=O)N1CCCC1N1NC1(c1ccccc1)C(F)(F)F] | 50 |
| I | 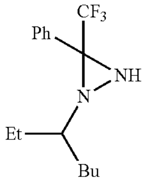 | 87 |
| J | 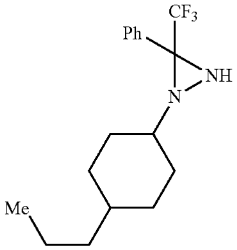 [SMILES: CCCC1CCC(N2NC2(c2ccccc2)C(F)(F)F)CC1] | 70 |
| K | 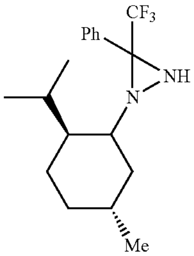 [SMILES: CC(C)[C@@H]1CC[C@@H](C)CC1N1NC1(c1ccccc1)C(F)(F)F] | 82 (dr = 4.5:1) |
| L | 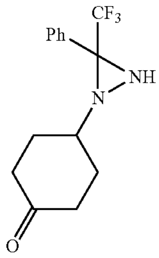 [SMILES: O=C1CCC(N2NC2(c2ccccc2)C(F)(F)F)CC1] | 42 |

TABLE 1-continued
| Compounds of Formula III Prepared by Above Process | | |
|---|---|---|
| Entry | Compound | Yield (%) |
| M | 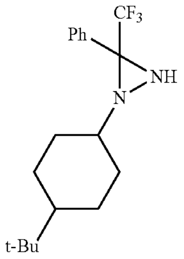 [SMILES: CC(C)(C)C1CCC(N2NC2(c2ccccc2)C(F)(F)F)CC1] | 86 |
| N | 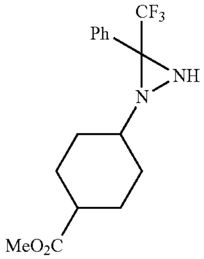 [SMILES: COC(=O)C1CCC(N2NC2(c2ccccc2)C(F)(F)F)CC1] | 76 |
| O | 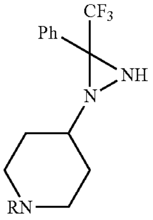 | R = Ts; 76% (one-pot: 58%; gram scale: 56%) R = Cbz; 79% R = Boc; 49% |
| P | 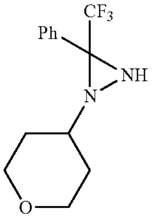 [SMILES: FC(F)(F)C1(c2ccccc2)NN1C1CCOCC1] | 71 |
| Q | 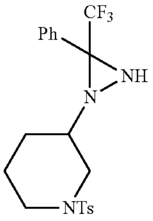 [SMILES: Cc1ccc(S(=O)(=O)N2CCCC(N3NC3(c3ccccc3)C(F)(F)F)C2)cc1] | 79 |
| R | 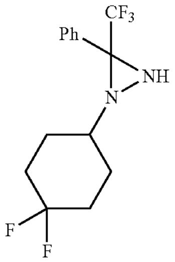 | 53 |

TABLE 1-continued
| Compounds of Formula III Prepared by Above Process | | |
|---|---|---|
| Entry | Compound | Yield (%) |
| S | 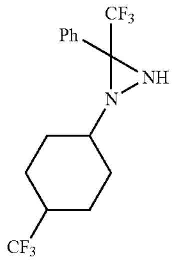 | 73 |
| T | 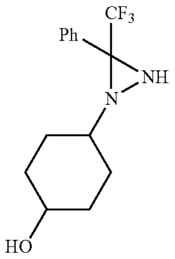 [SMILES: OC1CCC(N2NC2(c2ccccc2)C(F)(F)F)CC1] | 59 |
| U | 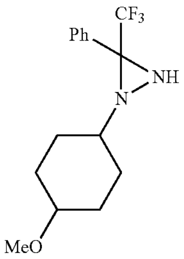 | 83 |
| V | 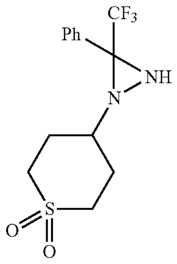 [SMILES: O=S1(=O)CCC(N2NC2(c2ccccc2)C(F)(F)F)CC1] | 69 |
| W | 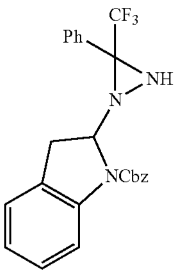 [SMILES: O=C(OCc1ccccc1)N1c2ccccc2CC1N1NC1(c1ccccc1)C(F)(F)F] | 78 |
| X | 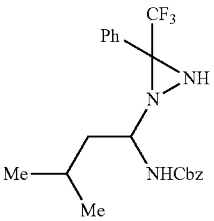 [SMILES: CC(C)CC(NC(=O)OCc1ccccc1)N1NC1(c1ccccc1)C(F)(F)F] | 65 |

TABLE 1-continued
Compounds of Formula III Prepared by Above Process
| Entry | Compound | Yield (%) |
|---|---|---|
| Y | 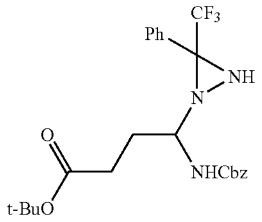 [SMILES: CC(C)(C)OC(=O)CCC(NC(=O)OCc1ccccc1)N1NC1(c1ccccc1)C(F)(F)F] | 50 (from N-protected glutamic acid) |
| Z | 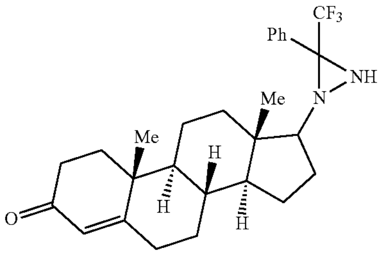 | 58 (from progesterone) |
| AA | 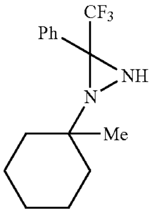 [SMILES: CC1(N2NC2(c2ccccc2)C(F)(F)F)CCCCC1] | 80% (3 equivalents of diazirine) |
| BB | 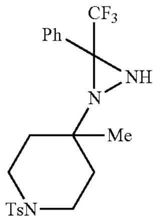 [SMILES: Cc1ccc(S(=O)(=O)N2CCC(C)(N3NC3(c3ccccc3)C(F)(F)F)CC2)cc1] | 75% (3 equivalents of diazirine) |
| CC | 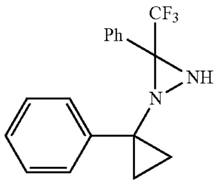 [SMILES: FC(F)(F)C1(c2ccccc2)NN1C1(c2ccccc2)CC1] | 46% (3 equivalents of diazirine) |
| DD | 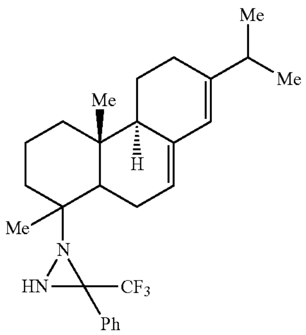 | 70% dr = 2.5:1 (3 equivalents of diazirine) (from abietic acid) |

TABLE 1-continued
| Compounds of Formula III Prepared by Above Process | | |
|---|---|---|
| Entry | Compound | Yield (%) |
| EE | 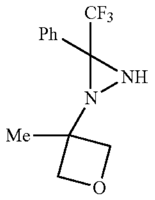 [SMILES: CC1(N2NC2(c2ccccc2)C(F)(F)F)COC1] | 96% (3 equivalents of diazirine) 74% (1.5 equivalents of diazirine) |
| FF | 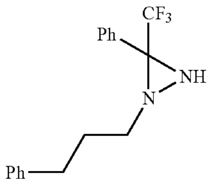 [SMILES: FC(F)(F)C1(c2ccccc2)NN1CCCc1ccccc1] | 80 |
| GG | 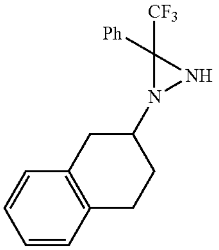 [SMILES: FC(F)(F)C1(c2ccccc2)NN1C1CCc2ccccc2C1] | 73 |
| HH | 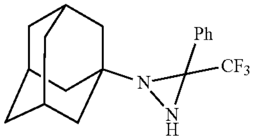 [SMILES: FC(F)(F)C1(c2ccccc2)NN1C12CC3CC(CC(C3)C1)C2] | 86 |
| II | 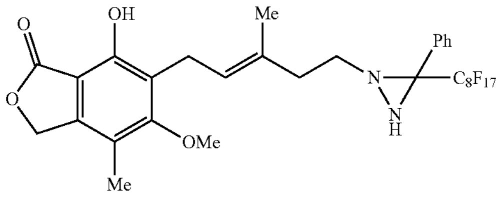 | 46 (from mycophenolic acid) |
| JJ | 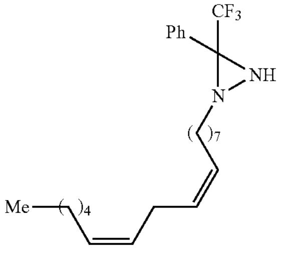 | 50 (from linoleic acid) |

Further representative examples of compound prepared by the above process are provided in Table 2.
TABLE 2
Further Compounds of Formula III Prepared by Above Process
| Entry | Compound | Yield (%) |
|---|---|---|
| KK | 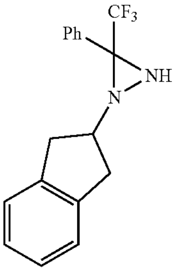 [SMILES: FC(F)(F)C1(c2ccccc2)NN1C1Cc2ccccc2C1] | 52 |
| LL | 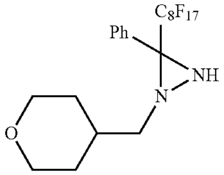 | 69 |
| MM | 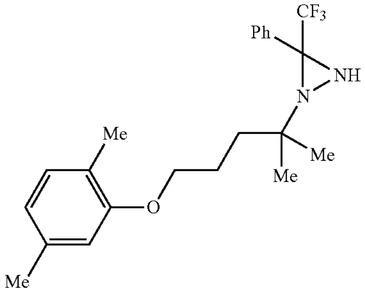 [SMILES: Cc1ccc(C)c(OCCCC(C)(C)N2NC2(c2ccccc2)C(F)(F)F)c1] | 66 (from gemfibrozil) |
| NN | 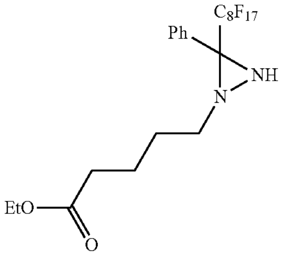 | 47% (from adipic acid) |
| OO | 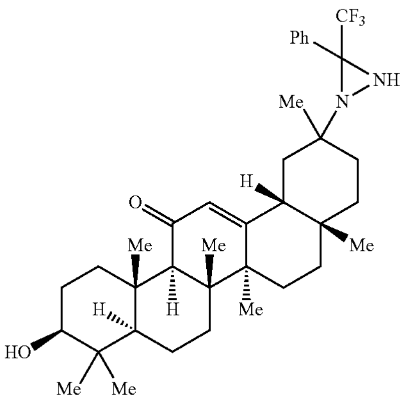 | 44 (from glycerrhetinic acid) |

In other embodiments, a process is provided for the synthesis of a compound of Formula III, or a salt or other suitable derivative thereof, the process comprising:

providing a compound of Formula IV:

(IV)

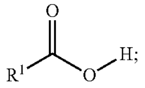

or a salt or suitable derivative thereof, wherein all variables are as defined herein;

providing a compound of Formula II;

and contacting and reacting the compound of Formula I with the compound of Formula II under irradiation of light having a wavelength from about 450 nm to about 490 nm in the presence of a photocatalyst, a base, and a disulfide to provide the compound of Formula III.

In some embodiments, the photocatalyst is an organic photocatalyst. In some embodiments, the organic photocatalyst is an acridinium photocatalyst. In some embodiments, the photocatalyst is

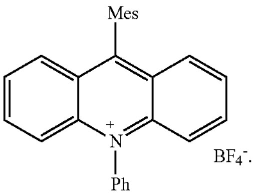

In some embodiments, the base is an organic amine base. In some embodiments, the base is 1,8-diazabicyclo[5.4.0]undec-7-ene.

In some embodiments, the disulfide is $(PhS)_2$.

Exemplary, non-limiting embodiments of the above described process are provided in Scheme 1 and Scheme 2 below.

Scheme 1

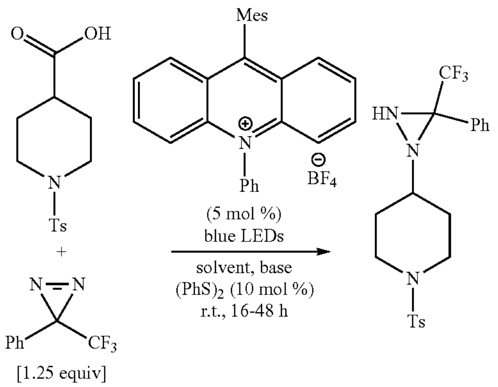

| Entry | Solvent/Base | Yield (%) |
|---|---|---|
| 1 | MeCN/lutidine | 0% |
| 2 | MeCN/DIPEA | trace |
| 3 | MeCN/DBU | 69% |
| 4 | $MeOH/H_2O$ (9:1), DBU | 33% |
| 5 | $MeCN/H_2O$ (9:1), DBU | 41% |

Scheme 2

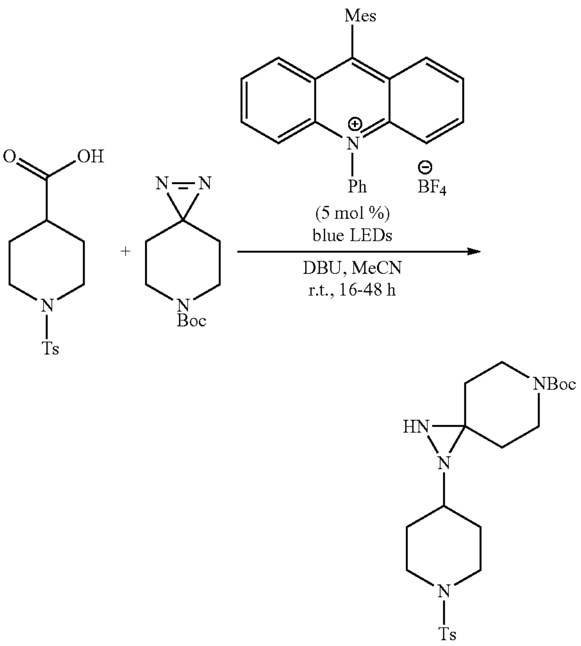

In other embodiments, a process is provided for the synthesis of a compound of Formula III, or a salt or other suitable derivative thereof, the process comprising:

providing a compound of Formula I;

providing a compound of Formula II:

and contacting and reacting the compound of Formula I with the compound of Formula II under irradiation of light having a wavelength from about 450 nm to about 490 nm in the presence of a phosphine compound and sodium iodide. In some embodiments, the phosphine compound is triphenylphosphine.

An exemplary, non-limiting embodiment of the above process is provided in Scheme 3 below.

Scheme 3

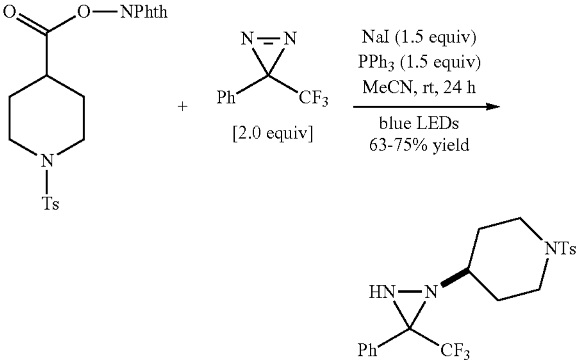

Products for Use in Processes

In another aspect of the present invention, compounds are also provided that may be used in the above synthetic processes. In particular, perfluoroalkyl-substituted diazirines are provided that can be used in the above process.

Thus, the invention also includes a compound of Formula II-a:

(II-a)

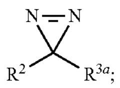

or a salt or other suitable derivative thereof; wherein:

$R^{3a}$ is $C_4$-$C_{14}$ perfluoroalkyl, and all other variables are as defined herein.

In some embodiments, $R^2$ is aryl. In some embodiments, $R^2$ is phenyl.

In some embodiments, $R^{3a}$ is $C_4$-$C_{14}$ perfluoroalkyl. In some embodiments, $R^{3a}$ is $C_4F_9$. In some embodiments, $R^{3a}$ is $C_5F_{11}$. In some embodiments, $R^{3a}$ is $C_6F_{13}$. In some embodiments, $R^{3a}$ is $C_7F_{15}$—In some embodiments, $R^{3a}$ is $C_8F_{17}$—In some embodiments, $R^{3a}$ is $C_9F_{19}$. In some embodiments, $R^{3a}$ is $C_{10}F_{21}$. In some embodiments, $R^{3a}$ is $C_{11}F_{23}$. In some embodiments, $R^{3a}$ is $C_{12}F_{25}$. In some embodiments, $R^{3a}$ is $C_{13}F_{27}$. In some embodiments, $R^{3a}$ is $C_{14}F_{29}$.

In some embodiments, the compound of Formula II-a is

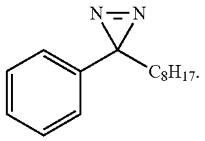

Preparation of Compounds of Formula I and Formula II

The compounds of Formula I and Formula II as used in the process described herein may be readily synthesized using methods known to those having skill in the art. Representative examples of such methods are provided below that are meant to be illustrative and not necessarily inclusive of all of the aspects of the subject matter described herein.

In one non-limiting aspect, a compound of Formula I may be synthesized by reacting a compound of Formula IV as described herein with N-hydroxyphthalimide or N-hydroxytetrachlorophthalimide in the presence of N,N-dimethylaminopyridine and an amide coupling reagent. In some embodiments, the amide coupling reagent is N,N'-diisopropylcarbodiimide. In another aspect, the amide coupling reagent is N,N'-dicyclohexylcarbodiimide. A representative, non-limiting example of a set of general conditions for the preparation of a compound of Formula I is provided in Scheme 4 below.

Scheme 4

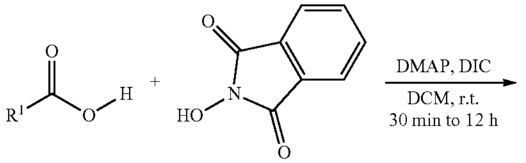

-continued

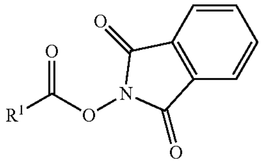

A representative example of a method for the synthesis of a compound of Formula II is provided in Scheme 5 below.

Scheme 5

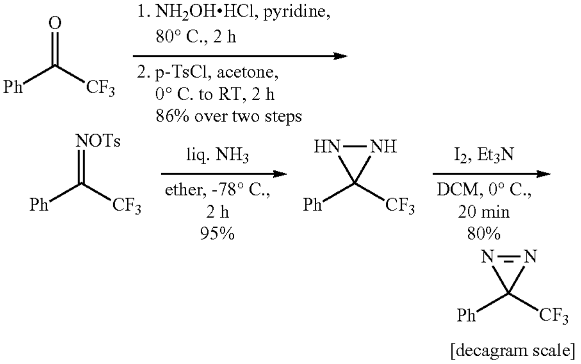

Other methods for the preparation of diazirines are known in the art and have been described previously.

Use of Reaction Products

The compounds of Formula III as formed by the process described herein may be further modified as would be deemed suitable for their intended purpose. Representative examples of methods that may be used to modify the compounds of Formula III as formed by the process described herein are provided below and are meant to be illustrative rather than inclusive. These examples are not intended to exclude equivalents and variations which would be apparent to one skilled in the art.

The diaziridine compound of Formula III as formed by the process described herein may be readily converted to an amine product by reaction with hydroiodic acid. Alternatively, this reaction may be performed with hydrochloric acid in the presence of molecular iodine or with hydrochloric acid in the presence of sodium iodide. A representative example of such a process is provided below in Scheme 6.

Scheme 6

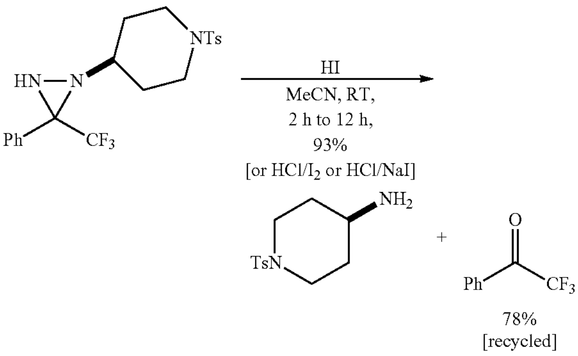

The diaziridine compound of Formula III as formed by the process described herein may be readily converted to a hydrazide product by reaction with a strong acid, including but not limited to methanesulfonic acid, sulfuric acid, or p-toluenesulfonic acid. A representative example of such a process is provided below in Scheme 7.

Scheme 7

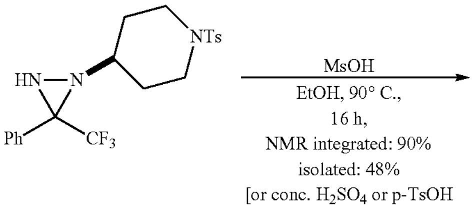

-continued

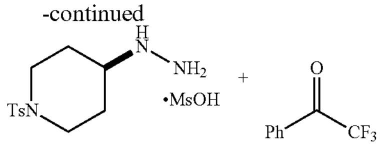

The diaziridine compound of Formula III as formed by the process described herein may be converted into a heterocycloalkyl or heteroaryl functional group by methods as would be known to those skilled in the art. Representative, but non-limiting, examples of such transformations are provided below in Scheme 8:

Scheme 8

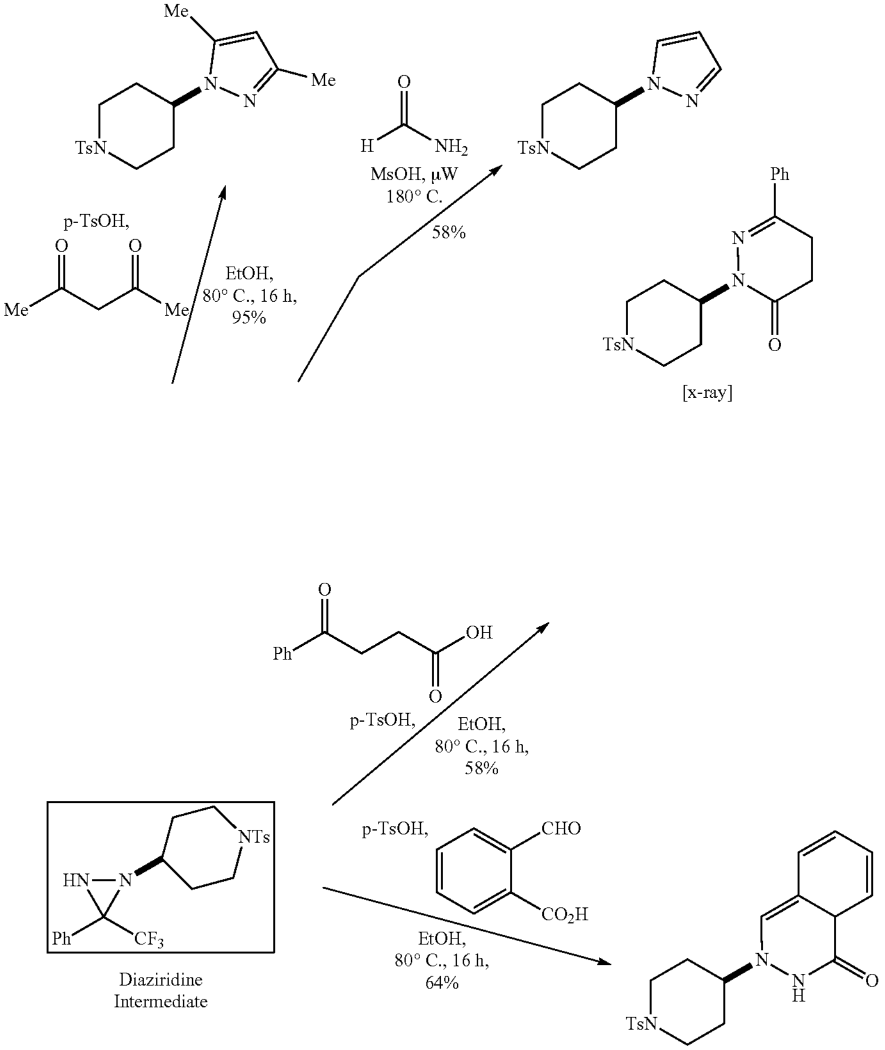

Diaziridine
Intermediate

-continued

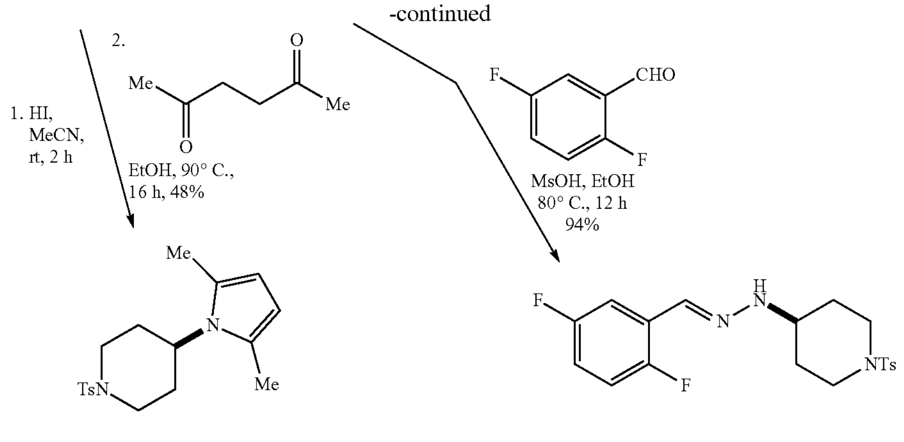

Fluorous Separation of Reaction Products and Byproducts

In another aspect of the present invention, methods are provided for the separation and recovery of by-products from the above described processes. In particular, if a diazirine compound of Formula II-a is used in the methods described herein, both the reaction product and the corresponding ketone byproduct may be separated from the other reaction mixture components by being sequestered into a fluorous phase. The fluorous phase may be either a fluorinated solvent or may be another fluorous separation system such as fluorous solid phase extraction (F-SPE). F-SPE cartridges consist of silica gel bonded with perfluoroalkyl groups and are commercially available (e.g., FluoroFlash® SPE cartridges). A fluorophobic solvent (typically 80:20 methanol/water) is used to elute any by-products of the reaction lacking a fluoroalkyl group through the SPE cartridge while the other groups are retained. The fluorous compounds can then be washed off the F-SPE cartridge using a fluorophilic solvent such as methanol, tetrahydrofuran, or acetone. A representative example of such a separation method being applied to the processes described herein is provided below in Scheme 9. As can be seen, the product of the first reaction step can be isolated alone cleanly using F-SPE by being retained on the F-SPE cartridge while all other reaction by-products are washed away. In the second step, the perfluoroalkylketone reaction by-product is instead retained on the F-SPE cartridge while the desired product is eluted. This allows recycling of the perfluoroalkylketone that is used to synthesize the diazirine reactants in the processes described herein.

As used herein, "fluorophobic" refers to compounds which tend to repel or fail to mix with other compounds containing one or more fluoro functional groups. As used herein, "fluorophilic" refers to compounds which tend to mix with or dissolve in other compounds containing one or more fluoro functional groups.

Scheme 9

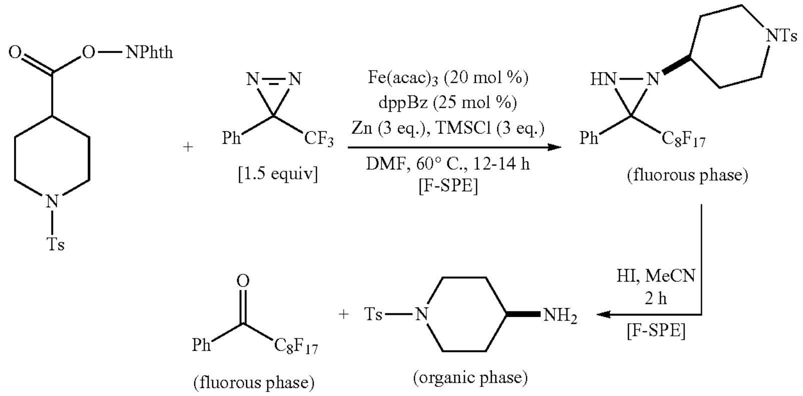

Thus in an alternative aspect,

Thus, a process is provided for the synthesis of a compound of Formula III-a:

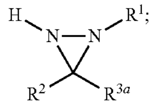

or a salt or other suitable derivative thereof, the process comprising:

providing a compound of Formula I:

(I)

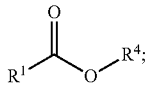

or a salt or other suitable derivative thereof;

providing a compound of Formula II:

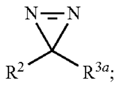

contacting and reacting the compound of Formula I with the compound of Formula II in the presence of an iron catalyst, a phosphine ligand, and a reductant at a temperature from about 70° C. to about 90° C. to provide a reaction mixture comprising the compound of Formula III-a and one or more byproducts lacking a fluoroalkyl group;

contacting a solid phase containing fluoroalkyl groups with the reaction mixture;

washing the solid phase with a fluorophobic solvent to elute the one or more byproducts lacking a fluoroalkyl group; and washing the solid phase with a fluorophilic solvent to elute the compound of Formula III-a;

wherein all variables are as defined herein.

In another alternative aspect, a process is provided for the synthesis of a compound of Formula V:

(V)

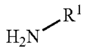

the process comprising:

contacting a compound of Formula III-a:

(III-a)

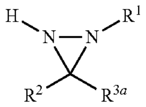

or a salt or other suitable derivative thereof, with a source of iodide anion under acidic conditions to form a reaction mixture containing the compound of Formula V and a compound of Formula VI:

(VI)

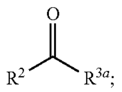

contacting a solid phase containing fluoroalkyl groups with the reaction mixture;

washing the solid phase with a fluorophobic solvent to elute the compound of Formula V; and optionally washing the solid phase with a fluorophilic solvent to elute the compound of Formula VI;

wherein all variables are as defined herein.

In some embodiments, the source of iodide anion comprises hydroiodic acid. In some embodiments, the source of iodide anion comprises molecular iodine. In some embodiments, the source of iodide anion comprises an iodide salt, for example sodium or potassium iodide. In some embodiments, the acidic conditions may be formed by the presence of hydrochloric acid or sulfuric acid.

In another alternative aspect, a process is provided for the synthesis of a compound of Formula VII:

(VII)

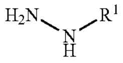

the process comprising:

contacting a compound of Formula III-a:

(III-a)

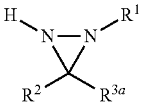

or a salt or other suitable derivative thereof, with an acid to form a reaction mixture containing the compound of Formula VII and a compound of Formula VI:

(VI)

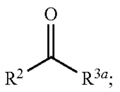

contacting a solid phase containing fluoroalkyl groups with the reaction mixture;

washing the solid phase with a fluorophobic solvent to elute the compound of Formula V; and optionally washing the solid phase with a fluorophilic solvent to elute the compound of Formula VI;

wherein all variables are as defined herein.

In some embodiments, the acid may comprise methanesulfonic acid, p-toluene sulfonic acid, or sulfuric acid.

In some embodiments, the solid phase containing fluoroalkyl groups comprises perfluoroalkylated silica gel.

In some embodiments, the fluorophobic solvent may comprise aqueous methanol. In some embodiment, the fluorophobic solvent may comprise 80:20 methanol:water.

In some embodiments, the fluorophilic solvent may comprise anhydrous methanol, acetone, or tetrahydrofuran. In some embodiments, the fluorophilic solvent may comprise anhydrous methanol.

EXAMPLES

The methods and compositions of the appended claims are not limited in scope by the specific methods and compositions described herein, which are intended as illustrations of a few aspects of the claims, and any methods and compositions that are functionally equivalent are within the scope of this disclosure. Various modifications of the methods and compositions in addition to those shown and described herein are intended to fall within the scope of the appended claims. Further, while only certain representative methods, compositions, and aspects of these methods and compositions are specifically described, other methods and compositions and combinations of various features of the methods and compositions are intended to fall within the scope of the appended claims, even if not specifically recited. Thus, a combination of steps, elements, components, and constituents can be explicitly mentioned herein; however, all other combinations of steps, elements, components, and constituents are included, even though not explicitly stated.

Example 1

Decarboxylative Amination: Diazirines as Single and Double Nitrogen Transfer Reagents The selective transfer of heteroatoms is a powerful tool in organic synthesis that allows for the rapid conversion of inexpensive commercial feedstocks to high value scaffolds for use in medicine, agrochemistry, chemical biology, and materials science. One general class of heteroatom transfer reagents with broad utility are three-membered strained heterocycles (FIG. 1A). Dioxiranes (1) are often used for C—H oxidations to afford site-selectivity that is difficult or impossible to match with other methods. New applications for oxaziridines (2) are regularly reported; they are able to transfer either their nitrogen or oxygen depending on the reagent structure and reaction conditions. Both oxaziridiniums and diaziridiniums (3) have been more recently developed as practical reagents. Like oxaziridines, they may be used for either oxidation or amination. Diazirines (4), which are extensively used as carbene sources in chemical biology, are notably lacking among this series of heterocycles with respect to heteroatom transfer. While scattered reports exist in the literature that demonstrate the ability for diazirines to act as an electrophilic source of nitrogen, it is apparent that none leverage the full potential of these reagents.

Figure 1B:
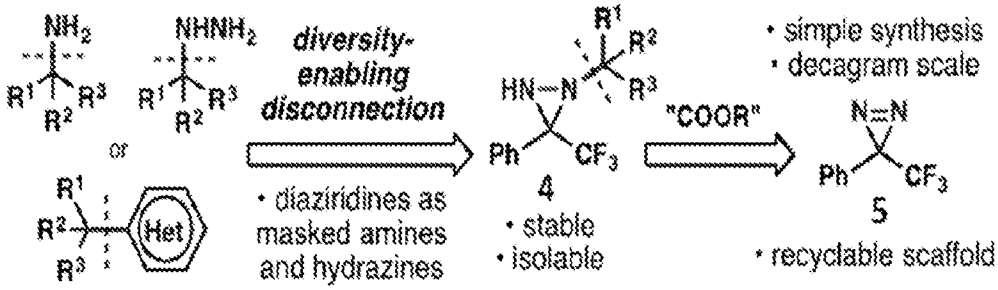

As partly evidenced by their widespread utility in synthetic organic chemistry, chemical biology, and proteomics, diazirines are simple to prepare and their synthesis can be conducted on a relatively large scale that lends itself well to reagent development (FIG. 1B). In principle, the monofunctionalization of diazirine (5) with a carboxylic acid equivalent would afford diaziridine (4). This structure, while generally stable and isolable, can be converted to amines, hydrazines, and a variety of nitrogen-containing heterocycles. Considered in a retrosynthetic manner, the use of diaziridine intermediates represents a "diversity-enabling disconnection", since diaziridine (4) may be thought of as both a masked amine and masked hydrazine. Herein, the present example outlines the discovery, development, and application of diazirines as practical amination reagents for the synthesis of amines, hydrazines, and nitrogen-containing heterocycles. This work lays the foundation for a new class of strain-driven reagents that can be used to rapidly forge C—N bonds on simple and complex scaffolds alike.

Reaction Development, Scope, and Late-Stage Functionalization

Figure 2A:
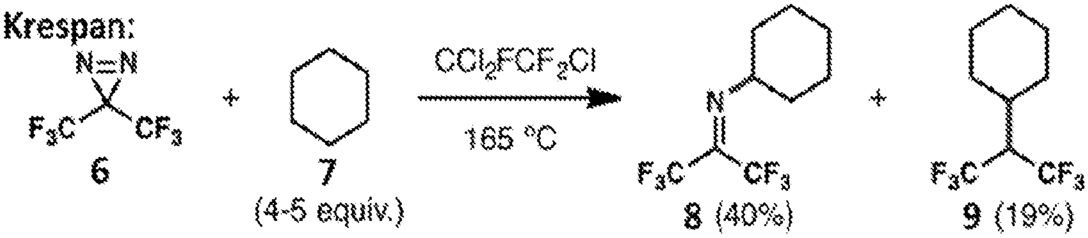

The initial investigation of diazirines as amination reagents was inspired by the work of Krespan and Barton, both of whom found that diazirines could react with alkyl radicals to form imines. Diazirine (6), upon heating to 165° C. with an excess of cyclohexane (7), afforded a modest amount of imine (8) in addition to the typical carbene insertion product (9) (FIG. 2A). A more detailed study was later reported by Barton, where his eponymous thiohydroxamate ester (10) was found to react with diazirine (11) to afford a mixture of imine (12) and sulfide (13) (FIG. 2B). Unless a large excess of diazirine (11) was used (twenty equivalents), sulfide (13) was found to be the major product along with low yields of imine (12). Notably, these precedents lacked both practicality and what are viewed as the critical ability to retain both nitrogen atoms in the initial adduct. Thus, several significant challenges needed to be addressed in order to develop a practical diazirine-based amination: (i) replacement of the photo- and thermally-labile thiohydroxamate ester (10) with a more bench-stable radical precursor, (ii) avoidance of either uncontrolled photochemical conditions or excessive heating that would be expected to convert the diazirine to its corresponding carbene, (iii) reduction of the equivalents of diazirine required from approximately twenty (in Barton's chemistry) to three or less, and, most importantly, (iv) avoidance of imine formation and retention of both nitrogen atoms in the form of a diaziridine intermediate.

Toward this end, N-(acyloxy)phthalimides, commonly referred to as redox-active esters, were employed as a precursor for the alkyl radicals. Redox-active esters have exploded in popularity in recent years, finding numerous applications in carbon-carbon and carbon-heteroatom bond formation. Among the many advantages of redox active esters are their simple and rapid preparation from ubiquitous carboxylic acids, ease of purification, and high bench-stability. Furthermore, they may be converted to the corresponding alkyl radicals under either transition-metal catalyzed or photochemical conditions. Despite their obvious advantages, the use of RAE's in C—N bond formation has been limited. Diazirine (15) was conveniently prepared in a high-yielding, four-step sequence on decagram scale.

Exploration of the decarboxylative amination began with nickel-catalyzed conditions employing piperidine derivative (14) with diazirine (15) (FIG. 2C). While no amination product was observed with $NiCl_2$-glyme/19 (entry 1), a 50% yield of diaziridine (17) was obtained with $NiCl_2 \cdot 6H_2O$/19. Importantly, no trace of imine (18) was observed in the reaction mixture. In an attempt to improve the yields, the catalyst was changed to $Fe(acac)_3$ and the reaction screened with phosphine ligands (16 and 20-22), varying amounts of Zn/TMSCl, and a chlorinated redox-active ester (TCNHPI) (entries 3-9). While the highest yield (76%) was observed with dppBz (16), dppb (22) was found to be an inexpensive alternative with only a modest decrease in yield. In cases where the redox-active ester was prone to hydrolysis under the reaction conditions, $FeCl_3 \cdot 6H_2O$ was found to increase stability and lead to an improved yield of the diaziridine (17) (entry 6). Critically, the use of diazenes (23) or (24), perhaps the most commonly used electrophilic amination reagents for the synthesis of hydrazines, in place of diazirine (15) did not afford any corresponding amination products (entries 10-11). Instead, only reduction of the diazene was observed under various conditions. Lastly, contrary to all expectations, similar yields could be obtained without running the reaction under strict precautions, such as an inert atmosphere, anhydrous conditions, and protection from ambient light (entry 12).

With optimized conditions in hand, the scope of the amination was explored with a wide variety of primary, secondary, and tertiary carboxylic acids (see Tables 1 and 2 and FIG. 3). The required redox-active esters were prepared in generally high yields by treatment of the carboxylic acids with N-hydroxyphthalimide in the presence of N,N'-diisopropylcarbodiimide (DIC) and 4-(dimethylamino)pyridine (DMAP) in multigram quantities. The decarboxylative amination was successful with either cyclic or acyclic hydrocarbons and heterocycles such as tetrahydrofuran (Entries F, G), piperidine (Entries O, Q, BB), tetrahydropyran (Entries P and LL), tetrahydrothiopyran (Entry V), indoline (Entry W), and oxetane (Entry EE). The observed functional group tolerance was quite broad: difluoro (Entries B, R) and trifluoromethyl groups (Entry S), carbamates (Entries H, O, W, X, Y), alcohols (Entries T, II, OO), ketones (Entry L), sulfones (Entry V), ethers (Entries U, II, MM), esters, (Entries N, Y, NN), enones (Entries Z, OO), olefins (Entries DD, II, JJ), and lactones (Entry II) were all tolerated. Highly sterically hindered bonds were formed with relative ease as shown in a menthol derivative (Entry K) and numerous tertiary systems (Entries AA, BB, CC, DD, EE, HH, MM, OO). The reaction was also useful for preparing orthogonally protected mixed aminals such as indoline (Entry W) and glutamic acid (Entry Y). The late-stage functionalization of complex natural products and pharmaceuticals was achieved with progesterone (Entry Z), mycophenolic acid (Entry II), gemfibrozil (Entry MM), glycerrhetinic acid (Entry OO), and abietic acid (Entry DD).

The reaction of primary redox-active agents with the trifluoromethyl-substituted diazirine proved to be challenging. Despite extensive attempts at optimization, including the use of large excesses of diazirine, low yields or no reaction was observed with most substrates. To circumvent this problem, perfluorinated diazirine (substituted with —$C_8F_{17}$) was synthesized and tested under the usual reaction conditions. Gratifyingly, moderate to high yields were obtained for a variety of structurally distinct substrates (see Entries II, LL, NN).

Diversification and Heterocycle Synthesis

Figure 4A:
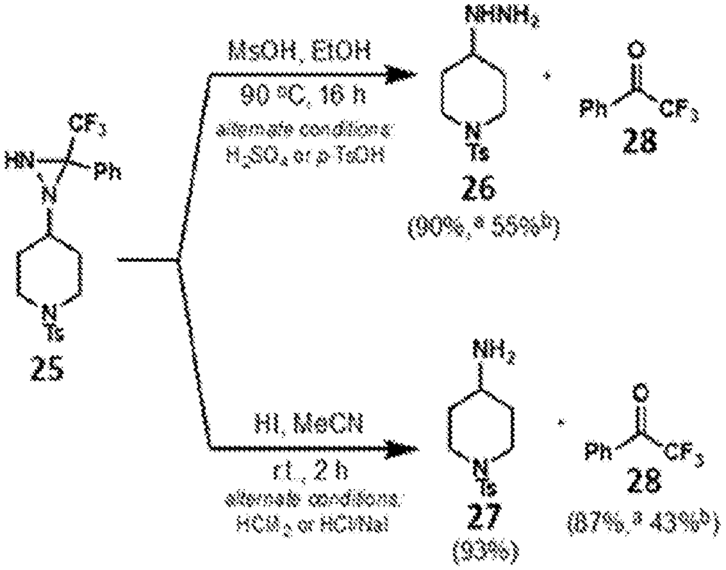
FIGS. 4A, 4B, and 4C depict the diversification and one-pot heterocyle syntheses using the diaziridines formed by the processes described herein.
Figure 4B:
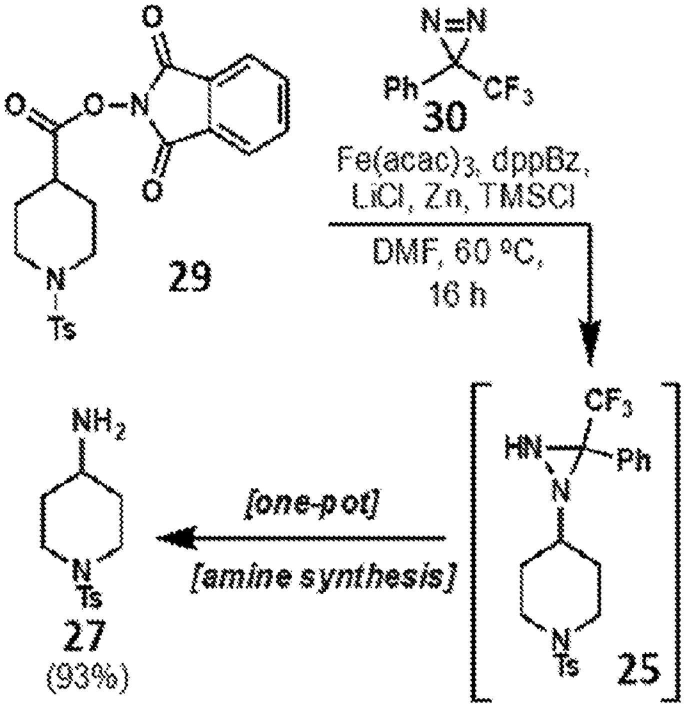
Figure 4C:
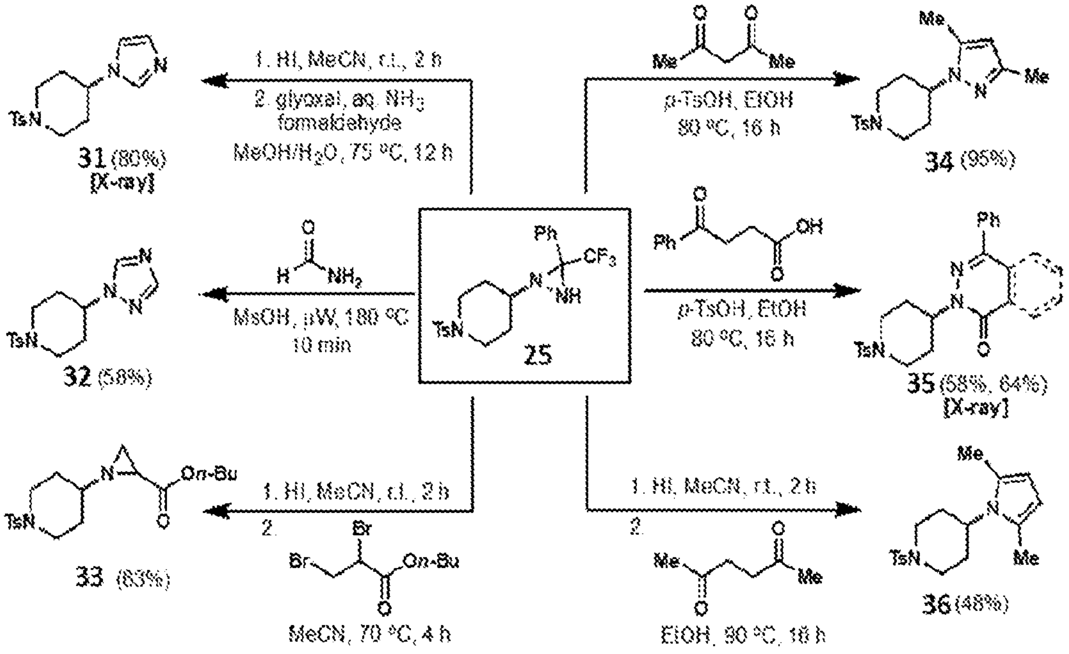
Figure 5A:
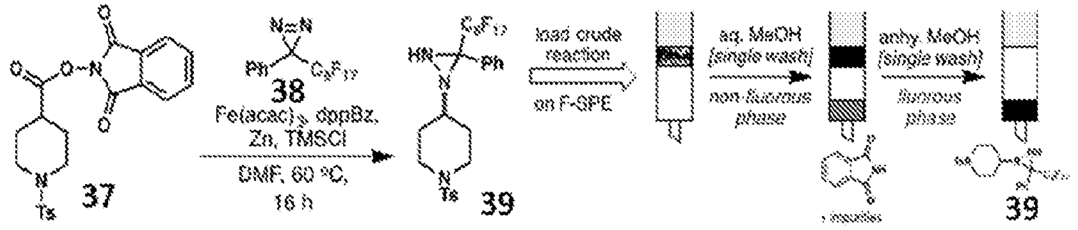
FIGS. 5A and 5B depict the application of the decarboxylative amination of redox-active esters with diazirines to fluorous phase synthesis.
Figure 5B:
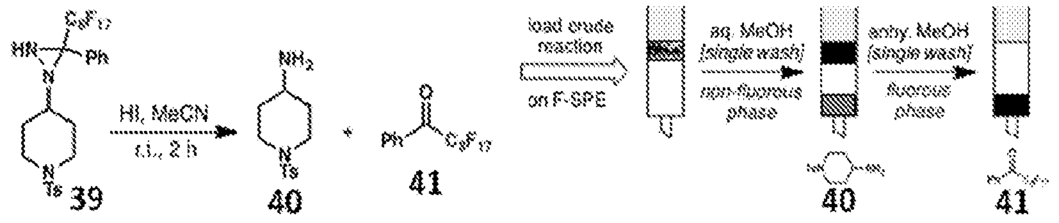

The utility and diversity of applications of the diazirine-based decarboxylative amination lies in the underexplored versatility of diaziridines (FIGS. 4A-C). By judicious choice of the reaction conditions, the diaziridine can be selectively hydrolyzed, leaving either one or both nitrogen atoms on the substrate. Thus, the diaziridines serve as "masked" amines or hydrazines and obviate the need for the troublesome purification of these highly polar compounds. Treatment of piperidine derivative (25) with MsOH in ethanol effects a hydrolysis reaction to afford hydrazine (26) in 90% yield. Upon purification as the mesylate salt, the yield of the hydrazine drops to 55%, highlighting the utility of the diaziridine approach which avoids purification. Instead, if the acid is coupled with a nucleophilic counterion (e.g. iodide), the hydrolysis occurs with concomitant N—N bond cleavage to afford amine (27) in near quantitative yield. For more sensitive substrates, a combination of LiCl/TMSCl may be used to convert the diaziridine to the amine In each of the cases, ketone (28) can be recovered and recycled into the diazirine reagent synthesis.

In order to further demonstrate the practical utility of the decarboxylative amination, the amine and hydrazine synthesis was then applied to a series of one-pot or telescoped syntheses of various medicinally-relevant heterocycles (FIG. 4C). To leverage the one-pot heterocycle synthesis via in situ generation of the corresponding hydrazines, N-tosylpiperidine diaziridine (25) was treated with either p-TsOH or MsOH followed by various carbonyl derivatives. In this manner, pyrazole (34) was obtained in 95% yield from 1,3-diketone in the presence of p-TsOH. Pyridazinone (35) and triazole (32) were obtained in a similar fashion from 1,4-diketone and formamide, respectively, both in 58% yield. In order to prepare heterocycles via the in situ generated amine, N-tosylpiperidine diaziridine (25) was treated with HI in MeCN, followed by addition of carbonyl or dibromide reagents to afford imidazole (31), pyrrole (36), and azetidine (33) in good yields.

Application to Fluorous Phase Synthesis

Fluorous phase synthesis comprises a family of techniques that were developed to simplify the separation and purification of solution phase reaction mixtures on the basis of fluorine content. Light fluorous phase chemistry requires a perfluorinated "tag" (typically $C_6F_{13}$ or $C_8F_{17}$) to be attached to the substrate (often via a protecting group) or the reagent/catalyst. After a given reaction, the perfluorinated molecules are easily separated from the non-perfluorinated components via fluorous solid-phase (F-SPE) extraction or other fluorous chromatographic methods. One of the main challenges in the successful use of fluorous phase synthesis is identifying a suitable site in the substrate or reagents to install the perfluorinated tag that avoids negatively impacting reactivity. Since the trifluoromethyl group was already successfully embedded in the diazirine, we postulated that the switch to the perfluoro group would maintain reactivity, and possibly enhance it. Furthermore, the inherent advantage in using the perfluorinated tag on the diazirine is that is allows for simplified purification in both stages of the amination: synthesis of the diaziridine and conversion to the corresponding amine, hydrazine, or heterocycles.

Under the standard reaction conditions, perfluorinated diazirine (38) was found to react smoothly with the redox-active ester (37). Upon completion of the reaction, the entire crude mixture was applied to the F-SPE cartridge and washed with a single aliquot of aqueous methanol (non-fluorous phase), which eluted all non-fluorous compounds and impurities such as N-hydroxyphthalimide and the catalyst/ligand system. A second wash with anhydrous methanol (fluorous phase) afforded pure perfluorinated diaziridine (39) in 88% yield. Perfluorinated diaziridine (39) was readily converted to amine (40) as previously described. Purification under F-SPE conditions furnished amine (40) in 78% yield in the non-fluorous phase wash, while ketone (41) was recovered in 88% yield in the fluorous phase wash. The use of perfluorinated diazirine (38) and its high yielding and high purity conversion to amine (40) with F-SPE demonstrates proof-of-concept for the use of diazirine-based aminations in high-throughput library synthesis.

General Experimental

Reagents were purchased at the highest commercial quality and used without further purification, unless otherwise stated. Anhydrous tetrahydrofuran (THF), dimethylsulfoxide (DMSO), acetonitrile (MeCN), dichloromethane (DCM), and N,N-dimethylformamide (DMF) were obtained by passing the previously degassed solvent through an activated alumina column (PPT Glass Contour Solvent Purification System) unless otherwise stated. Yields refer to chromatographically and spectroscopically ($^1$H NMR) homogeneous material, unless otherwise stated. Reactions were monitored by Liquid Chromatography Mass spectrometry (LC/MS) or Thin Layer Chromatography (TLC) carried out on 250 μm SiliCycle SiliaPlates (TLC Glass-Backed TLC Extra Hard Layer, 60 Å), using either of the visualizing agents such as shortwave UV light, iodine, or $KMnO_4$, CAM, ninhydrin or p-anisaldehyde with heat as developing agents. Flash column chromatography was performed with a Biotage Isolera One (ZIP or SNAP Ultra cartridges) or with traditional glass flash columns using SiliCycle Silia-Flash® P60 (particle size 40-63 μm). NMR spectra were recorded on a Bruker Ascend™ 500 MHz instrument and were calibrated using residual undeuterated solvent as an internal reference (Chloroform-d: 7.26 ppm $^{1}H$ NMR, 77.16 ppm $^{13}C$ NMR; DMSO-$d_6$: 2.50 ppm $^{1}H$ NMR, 39.5 ppm $^{13}C$ NMR). The following abbreviations were used to explain NMR peak multiplicities: s=singlet, d=doublet, t=triplet, q=quartet, dd=doublet of doublet, tt=triplet of triplet, ddt=doublet of doublet of triplet, m=multiplet, br=broad. High-resolution mass spectra (HRMS) were recorded on an Agilent 6230 LC/MS TOF mass spectrometer and 1200 Agilent LC-MS TOF 6230 (for perfluoro compounds) using electrospray ionization time-of-flight (ESI-TOF) reflection experiments. Melting points were recorded on a Chemglass DMP 100 melting point apparatus and were uncorrected.

Handling of Reagents

All the redox-active esters (RAEs) were stored in vials in a refrigerator at 0° C. All diazirines were stored in a vial at −20° C. under argon (Although the diazirines are moisture stable, this prevented water being introduced into subsequent reactions). The vial containing diazirine was covered with aluminum foil to avoid direct light. Iron (III) acetylacetone ($Fe(acac)_3$), 1,2-bis(diphenylphosphino)benzene (dppBz), zinc powder, and chlorotrimethylsilane (TMSCl) were stored on benchtop in the commercial bottles it came in. N, N-dimethylformamide (DMF) used for the catalytic reaction was dried over activated molecular sieves and stored in a flask attached with Ar balloon.

General Procedure: Synthesis of Redox-Active Esters

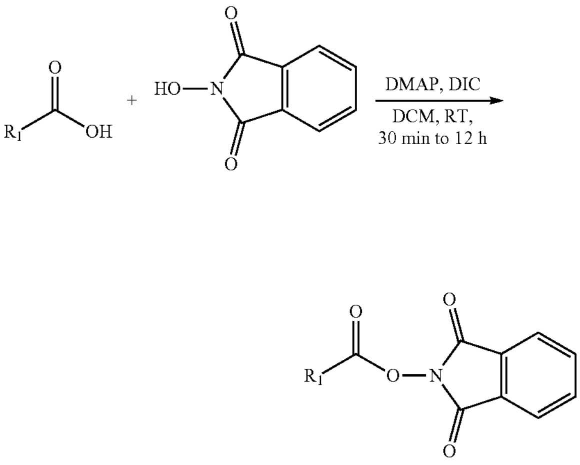

Redox-active esters were prepared according to a previously reported procedure. In short, a round-bottom flask or culture tube was charged with (if solid) carboxylic acid (1.0 eq.), N-hydroxyphthalimide (1.0-1.1 eq.) and 4-(dimethylamino)pyridine (DMAP) (0.1 eq.). DCM or THF was added (0.1 M), and the mixture was stirred vigorously. If liquid, carboxylic acid (1.0 eq.) was added via syringe. Diisopropylcarbodiimide (DIC) (1.1 eq.) was then added dropwise via syringe, and the mixture was allowed to stir until the acid was consumed (determined by TLC). Typical reaction times ranged between 0.5 h and 12 h. The mixture was filtered over Celite® and rinsed with additional DCM. The solvent was removed under reduced pressure and purification by column chromatography afforded the desired redox-active esters.

Synthesis of Diazarines

Synthesis of 3-Phenyl-3-(trifluoromethyl)-3H-diazirine

Step 1: Synthesis of N-Tosyloxime 1-3

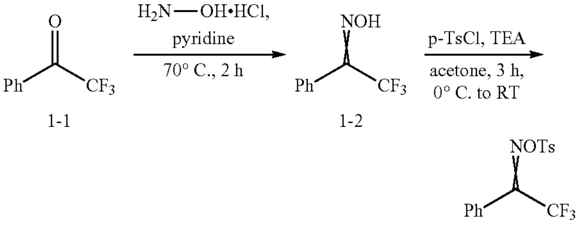

1-1 1-2 1-3

A 100 mL round bottom flask with a magnetic stir bar was charged with 2,2,2-trifluoromethylacetophenone, 1-1 (2.46 g, 14.1 mmol, 1 eq.). The flask was cooled to 0° C. and excess of pyridine (50 mL) followed by hydroxylamine hydrochloride (1.17 g, 16.9 mmol, 1.2 eq.) were added. This reaction mixture was stirred with heating for 2 h at 70° C. A drying tube was fitted on the top of the condenser during this time. After confirmation of disappearance of starting material by TLC, the reaction mixture was cooled down. The reaction mixture was then concentrated under reduced pressure and was treated with 2 M HCl (10 mL). The oxime 1-2 was then extracted with ethyl acetate (3×30 mL each). The combined organic fractions were washed with brine (40 mL), dried over $MgSO_4$ and solvent was evaporated under reduced pressure. The colorless oil obtained was used for the next step without further purification.

To a round bottom flask containing oxime 1-2, 100 mL of acetone was added and the flask was cooled to 0° C. To this solution 5.9 mL of triethylamine (4.28 g, 42.3 mmol, 3 eq.) was added at 0° C. and allowed to stir for 15 min. Next p-toluenesulfonyl chloride (p-TsCl) (3.23 g, 16.9 mmol, 1.2 eq.) was added portion-wise. The formation of a thick slurry was observed along with color change to orange. The ice bath was removed and the reaction was stirred vigorously for 3 h. After TLC confirmed the disappearance of the intermediate oxime 1-2, the volatiles were removed under reduced pressure to obtain a dry solid. This crude product was then dry loaded onto the column. The pure product, 1-3 was obtained by gradient elution of 10-30% ethyl acetate in hexanes and dried on a high vac system, resulting in a white solid (4.17 g, 86%). The product contains a mixture of E and Z isomers.

Physical state: White solid; $R_f$=0.27 (10% ethyl acetate in hexanes, vis UV); $^{1}H$ NMR: (500 MHz, Chloroform-d) δ 7.92-7.88 (m, 3H), 7.54-7.51 (m, 1.5H), 7.49-7.36 (m, 9.5H), 2.48 (s, 3H) (major diastereomer), 2.46 (s, 2H) (minor diastereomer); $^{13}C$ NMR: (126 MHz, Chloroform-d) δ 154.2 (q, $J_{C-F}$=33.0 Hz), 154.1 (q, $J_{C-F}$=32.0 Hz) 146.3, 146.2, 131.9, 131.7, 131.5, 131.3, 130.0, 129.4, 129.2, 128.9, 128.8, 128.5, 127.8, 124.7, 119.7 (q, $J_{C-F}$=277.4 Hz), 117.4 (q, $J_{C-F}$=283.2 Hz), 21.9, 21.8; $^{19}F$ NMR: (471 MHz, Chloroform-d) δ −61.50, −66.78; HRMS: Calculated for $C_{15}H_{13}F_3NO_3S$ 344.0563 [M+H$^+$]; found 344.0573.

Step 2: Synthesis of Diaziridine 1-4

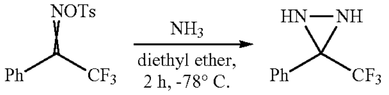

1-3 1-4

A 250 mL round bottom flask charged with a magnetic stir bar was marked with the volume of liquid ammonia required (20 mL). This flask was then either flame-dried or oven-dried, then cooled to room temperature under argon before cooling it to −78° C. Liquid ammonia was then condensed into the flask to the previously marked level. The N-tosyloxime 1-3 (2.22 g, 6.47 mmol, 1 eq.) was dissolved in dry diethyl ether (20 mL) and transferred to the flask containing liquid ammonia either by a syringe or a canula with stirring. The reaction mixture stirred for 2 h while the temperature was maintained at −78° C. to observe the formation of white precipitate. After two hours the TLC confirmed the disappearance of starting material. The reaction flask was carefully opened to atmosphere in the hood and the dry ice/acetone bath was removed. The reaction mixture was slowly allowed to come to room temperature over three hours to allow for evaporation of excess ammonia. (Caution: Forcing this process faster results in vigorous bubbling and loss of product splashing.) The product was extracted using diethyl ether (3×30 mL each) and combined ether layers were washed with water (40 mL), dried over $MgSO_4$ and then evaporated under reduced pressure to obtain the crude diaziridine 1-4 as a white solid after drying (1.16 g, 95%). This compound was used for the next step without any further purification. The compound sublimed on high vac system so the volatiles were evaporated under lower vacuum.

Physical state: White, low melting solid; $R_f$=0.21 (10% ethyl acetate in hexanes, vis. UV, iodine); $^1$H NMR: (500 MHz, Chloroform-d) δ 7.63-7.61 (m, 2H), 7.47-7.41 (m, 3H), 2.79 (d, J=8.4 Hz, 1H), 2.23 (d, J=8.6 Hz, 1H); $^{13}$C NMR: (126 MHz, Chloroform-d) δ 131.8, 130.3, 128.9, 128.3, 123.6 (q, $J_{C-F}$=278.3 Hz), 58.2 (q, $J_{C-F}$=35.8 Hz); $^{19}$F NMR: (471 MHz, Chloroform-d) δ-75.58; HRMS: Calculated for $C_8H_8F_3N_2$ 189.0364 [M+H$^+$]; found 189.0360.

Step 3. Synthesis of 3-Phenyl-3-(trifluoromethyl)-3H-diazirine (1-5)

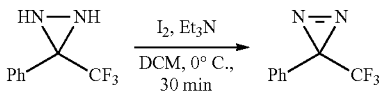

1-4 1-5

The dry diaziridine 1-4 (1.0 g, 5.31 mmol, 1 eq.) was transferred to a 100 mL flame-dried round bottom flask fitted with a magnetic stirbar under an argon balloon. To this reaction flask dry DCM (0.1-0.2 M) was added and the flask was cooled to 0° C. The flask along with the ice bath was covered with aluminum foil and the hood lights were turned off. To the reaction mixture, 1.63 mL of triethylamine (1.18 g, 11.7 mmol, 2.2 eq.) was added and allowed to stir for 10 minutes followed by pellet wise addition of $I_2$ (1.48 g, 5.84 mmol, 1.1 eq.). With every addition of a pellet of iodine the color changed from colorless to dark orange but disappeared within a few seconds. Iodine was added until the dark orange color persisted even after removing the ice bath. After the TLC confirmed the disappearance of starting material the reaction mixture was washed using sat. $Na_2S_2O_3$ to remove excess $I_2$ and then water or brine (30 mL). Extraction using DCM (2×30 mL) was carried out quickly in the dark to avoid degradation of the diazirine. The combined organic fractions were dried using $MgSO_4$ then evaporated under reduced pressure covered with aluminum foil. A flash column with n-pentane afforded the pure diazirine, 6, that was stored in an aluminum foil covered flask at −20° C. under argon atmosphere. The product obtained was colorless oil (0.80 g, 81%). Physical state: Colorless oil; $R_f$=0.76 (10% ethyl acetate in hexanes, vis. UV); $^1$H NMR: (500 MHz, Chloroform-d) 6 7.45-7.37 (m, 3H), 7.23-7.18 (m, 2H); $^{13}$C NMR: (126 MHz, Chloroform-d) δ 129.8, 129.3, 128.9, 126.6, 122.3 (q, $J_{C-F}$=274.7 Hz), 28.6 (q, $J_{C-F}$=40.4 Hz); $^{19}$F NMR: (471 MHz, Chloroform-d) δ-65.25; HRMS: Calculated for $C_8H_6F_3N_2$ 187.0478 [M+H$^+$]; found 187.0485.

Synthesis of Perfluoro Diazirine 2-6

Step 1: Synthesis of Ketone 2-2

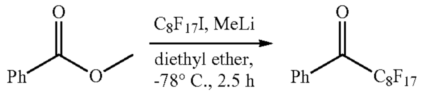

2-1 2-2

To a 500 mL round bottom flask, 1.84 mL methyl benzoate, 2-1 (2 g, 14.7 mmol, 1 eq.) and 150 mL of dry diethyl ether were added. Maintaining the 0.1 M concentration was crucial. To this solution, 4.32 mL of perfluorooctyl iodide (8.36 g, 17.64 mmol, 1.2 eq.), that was dried over 4 Å molecular sieves overnight was added. The reaction mixture was then cooled to −78° C. followed by addition of 10.1 mL of methyl lithium (1.6 M in diethyl ether, 16.2 mmol, 1.1 eq.) dropwise. After 2.5 h TLC confirmed the disappearance of methyl benzoate. The reaction was quenched by dropwise addition of sat. $NH_4Cl$ at 0° C. (addition at room temperature may result in decreased yield). The aqueous layer was extracted using diethyl ether (3×50 mL). The combined organic fractions were dried over $MgSO_4$, filtered and concentrated under reduced pressure. Purified the resulting ketone 2-2 by column chromatography on silica gel with gradient elution using 0-5% ethyl acetate in hexanes to obtain colorless oil (5.72 g, 74%).

Physical state: Colorless oil; $R_f$=0.75 (33% ethyl acetate in hexanes, vis. UV); $^1$H NMR: (500 MHz, Chloroform-d) δ 8.07 (dq, J=8.5, 1.2 Hz, 2H), 7.73-7.70 (m, 1H), 7.57-7.53 (m, 2H); $^{13}$C NMR: (126 MHz, Chloroform-d) δ 183.4 (t, $J_{C-F}$=26.1 Hz), 135.5, 131.7 (t, $J_{C-F}$=2.1 Hz), 130.4 (t, $J_{C-F}$=3.6 Hz), 129.2, 120.7 (t, $J_{C-F}$=36.44 Hz), 118.4 (t, $J_{C-F}$=33.0 Hz), 116.1 (t, $J_{C-F}$=33.0 Hz), 113.9-112.4 (m), 111.6-110.0 (m), 109.4-108.1 (m); $^{19}$F NMR: (471 MHz, Chloroform-d) δ-80.80 (t, J=10.0 Hz), −112.66--112.79 (m), −120.79--120.97 (m), −121.69--121.97 (m), −122.63--122.82 (m), −126.05--126.22 (m); HRMS: Calculated for $C_{15}H_6F_{17}O$ 525.0142 [M+H$^+$]; found 525.0177.

Step 2: Synthesis of N-Tosyloxime 2-4

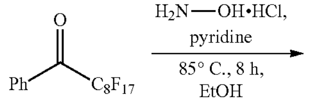

2-2

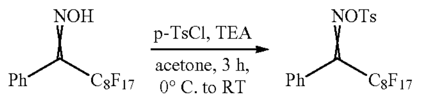

2-3 2-4

To a 250 mL round bottom flask, 2,2,3,3,4,4,5,5,6,6,7,7,8,8,9,9,9-heptadecafluoro-1-phenylnonan-1-one (7.34 g, 14.0 mmol, 1 eq.), ethanol (18 mL), and pyridine (36.3 mL, 448 mmol, 32 eq.) were added. To this stirring solution hydroxylamine hydrochloride (1.46 g, 21 mmol, 1.5 eq.) was added and mixture was heated at 85° C. for 8 h. After the ketone disappeared according to TLC, the reaction was cooled to room temperature and volatiles were concentrated under reduced pressure followed by dilution with water. The compound was extracted using DCM (3×30 mL) and then the combined organic layers were washed with water (30 mL) and brine (30 mL). The extracts were dried using $MgSO_4$ concentrated under reduced pressure. Light yellow viscous oil [$R_f$=0.32 (10% ethyl acetate in hexanes, vis. UV)] was obtained that was used for the next reaction without further purification.

The oxime 2-3 was dissolved in 50 mL acetone and to this, 5.8 mL of triethylamine (4.25 g, 42 mmol, 3 eq.) was added dropwise. This solution was cooled down to 0° C. and p-TsCl (3.20 g, 16.8 mmol, 1.2 eq.) was added portionwise. After 10 minutes at 0° C., the reaction was warmed to room temperature. The reaction mixture was stirred at room temperature for 3 h; during this time, white solid crashed out and the solution turned light orange. The solid was filtered; washed with additional acetone and concentrated under reduced pressure. Column chromatography on silica gel using gradient elution of 5-% ethyl acetate in hexanes afforded a mixture of cis-trans isomers (8.0 g, 83% over two steps) of N-tosyloxime 2-4.

Physical state: White solid; $R_f$=0.39 (10% ethyl acetate in hexanes, vis. UV); $^1H$ NMR: (500 MHz, Chloroform-d) δ 7.89-7.85 (m, 4H), 7.54-7.50 (m, 2H), 7.48-7.44 (m, 2H), 7.43-7.35 (m, 8H), 7.30-7.24 (m, 2H), 2.47 (s, 6H); $^{13}C$ NMR: (126 MHz, Chloroform-d) δ 155.6 (t, $J_{C-F}$=25.9 Hz), 153.8 (t, $J_{C-F}$=24.9 Hz), 146.3, 146.2, 131.7, 131.6, 131.5, 131.4, 130.0, 129.9, 129.6, 129.4, 129.3, 128.9, 128.8, 128.8, 128.5, 125.1, 120.7 (t, $J_{C-F}$=30.6 Hz), 118.4 (t, $J_{C-F}$=33.2 Hz), 116.1 (t, J=33.2 Hz), 115.0-114.0 (m), 113.8-112.0 (m), 111.5-109.9 (m), 109.3-108.0 (m), 106.7-105.8 (m), 21.9, 21.8; $^{19}F$ NMR: (471 MHz, Chloroform-d) δ-80.76 (t, J=10.2 Hz), −106.27--107.15 (m), −109.03--110.25 (m), −118.73 (dt, J=17.8, 7.6 Hz), −119.89 (dq, J=19.2, 7.8, 7.2 Hz), −120.92 (dd, J=21.9, 10.5 Hz), −121.41--121.73 (m), −122.70 (tt, J=19.4, 9.4 Hz), −126.11 (dt, J=14.0, 7.3 Hz); HRMS: Calculated for $C_{22}H_{13}F_{17}NO_3S$ 694.0339 [M+H$^+$]; found 694.0378.

Step 3: Synthesis of Diaziridine 2-5

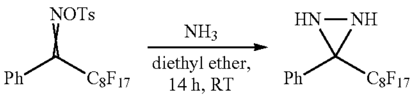

2-4 2-5

A 250 mL pressure tube was marked for a 40 mL volume, dried in an oven and then cooled to room temperature under argon. With an argon balloon on the pressure vial was cooled to −78° C. To the vial 40 mL of liquid $NH_3$ was condensed. A solution of N-tosyloxime 2-4 (2.02 g, 2.91 mmol, 1 eq.) in dry ether (40 mL) was added to the liquid ammonia. The pressure vial was sealed and allowed to come to room temperature and stirred overnight. After approximately 14 h, the reaction mixture was cooled to −78° C. and the cap of the vial was opened carefully. The reaction mixture was warmed to room temperature slowly to evaporate the excess ammonia. After the liquid ammonia was evaporated, water was added and extracted with diethyl ether (2×15 mL). The combined organic fractions were dried with $MgSO_4$, and concentrated under reduced pressure. The compound was dried on a high vac to obtain pure white solid, diaziridine 2-5 (1.5 g, quantitative). Physical state: White solid; $R_f$=0.25 (10% ethyl acetate in hexanes, vis. UV, iodine); $^1H$ NMR: (500 MHz, Chloroform-d) δ 7.60-7.59 (m, 2H), 7.44-7.39 (m, 3H), 2.81 (s, 1H), 2.24 (s, 1H); $^{13}C$ NMR: (126 Mz, Chloroform-d) δ 132.4, 130.3, 128.8, 128.8, 118.4 (t, $J_{C-F}$=34.0 Hz), 116.1 (t, $J_{C-F}$=40 Hz), 111.2-110.0 (m), 109.3-107.7 (m), 58.1; $^{19}F$ NMR: (471 MHz, Chloroform-d) δ-80.76 (t, J=10.1 Hz), −118.31, −118.83, −118.95, −119.36, −119.98, −121.53--122.05 (m), −122.60--122.83 (m), −123.50--123.66 (m), −124.07--124.24 (m), −126.04--126.21 (m); HRMS: Calculated for $C_{15}H_8F_{17}N_2$ 539.0444 [M+H$^+$]; found 539.0411.

Step 4: Synthesis of Diazirine 2-6

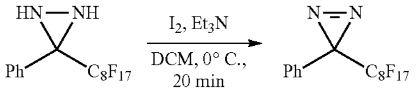

2-5 2-6

A 100 mL round bottom flask was flame-dried and then cooled under argon. To this flak, diaziridine 2-5 (1.19 g, 2.21 mmol, 1 eq.) was dissolved in dry DCM (25 mL). The solution was cooled to 0° C. followed by addition of 0.678 mL of triethylamine (0.492 g, 4.86 mmol, 2.2 eq.) The reaction flask was covered by aluminum foil and then iodine (0.62 g, 2.43 mmol, 1.1 eq.) was added pellet wise. With each addition of few pellets of iodine the color changed to yellow and disappeared. Iodine was added until the dark orange color persisted at room temperature for 10 minutes. The reaction was quenched by adding saturated sat. $Na_2S_2O_3$. The solution was diluted with water and extracted with DCM (3×15 mL). The combined the organic fractions were dried over $MgSO_4$, and concentrated under reduced pressure at room temperature in the dark. The compound 2-6 was purified by flash column chromatography on silica gel with n-pentane to obtain colorless oil at room temperature (white solid at −20° C.). Diazirine 2-6 was stored at −20° C. in a vial covered with aluminum foil. The yield for the reaction was 0.95 g, 80%.

Physical state: Colorless oil at room temp, white solid at −20° C.; $R_f$=0.65 (10% ethyl acetate in hexanes, vis. UV); $^{1}$H NMR: (500 MHz, Chloroform-d) δ 7.43-7.37 (m, 5H); $^{13}$C NMR: (126 MHz, Chloroform-d) δ 130.2, 129.4, 129.2, 128.4, 118.4 (t, $J_{C-F}$=33.2 Hz), 116.1 (td, $J_{C-F}$=32.6, 17.9 Hz), 113.9 (t, $J_{C-F}$=32.5 Hz), 111.8 (t, $J_{C-F}$=32.2 Hz), 111.4-110.0 (m), 109.1-108.1 (m), 27.9 (t, $J_{C-F}$=28.5 Hz); $^{19}$F NMR: (471 MHz, Chloroform-d) δ-80.82--80.89 (m), −109.42--109.56 (m), −120.08--120.27 (m), −121.71--122.10 (m), −122.66--122.89 (m), −126.09--126.29 (m); HRMS: Calculated for $C_{15}H_6F_{17}N_2$ 536.0181 [M]; found 536.0180.

General Procedure: Iron-Catalyzed Synthesis of Substituted Diaziridines

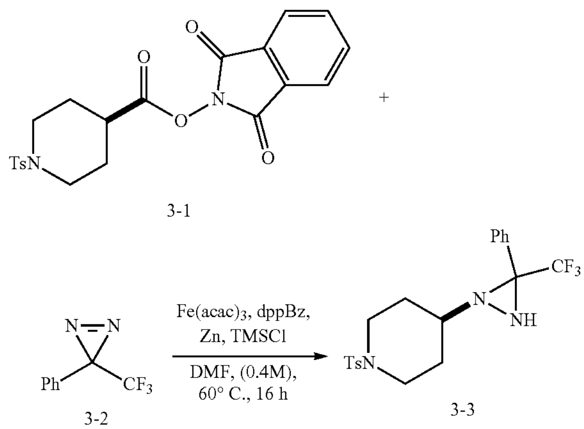

3-1

3-2

3-3

A culture tube fitted with rubber lined cap with a magnetic stir bar was flame-dried and cooled under an argon balloon. The redox-active ester 3-1 (43 mg, 0.1 mmol, 1 eq.) and Zn (20 mg, 0.3 mmol, 3 eq.) were added to the vial followed by back flushing with argon. In another small flame-dried reaction vial, $Fe(acac)_3$ (7.1 mg, 0.02 mmol, 20 mol %, 0.2 eq.) and dppBz ligand (11.2 mg, 0.025 mmol, 25 mol %, 0.25 eq.) were added under argon atmosphere. This catalyst system was dissolved in 0.3 mL dry DMF. After stirring for 10 minutes a homogeneous mixture was formed. To the dry reaction mixture of the RAE and Zn, TMSCl (38 μL, 0.3 mmol, 3 eq.) was added. This was followed by addition of catalyst using a syringe, followed immediately by addition of the diazirine 3-2 (0.028 g, 0.15 mmol, 1.5 eq.). After addition of all the reagents was complete, the vial was covered with aluminum foil and kept stirring on the pre-heated stir plate at 60° C. The reaction was heated overnight. After complete consumption of the RAE confirmed by TLC, the reaction was quenched with sat. $NH_4Cl$ (approx. 10 mL) and brine (30 mL). The solution was extracted using ethyl acetate (3×20 mL). The combined organic fractions were dried with $MgSO_4$, filtered and then concentrated under reduced pressure. The crude product was loaded on the silica gel and purified by a gradient elution of 0-20% ethyl acetate in hexanes. This yielded the pure product, compound 3-3, as a white solid (33.7 mg, 76%).

General Procedure: Nickel-Catalyzed Synthesis of Substituted Diaziridines

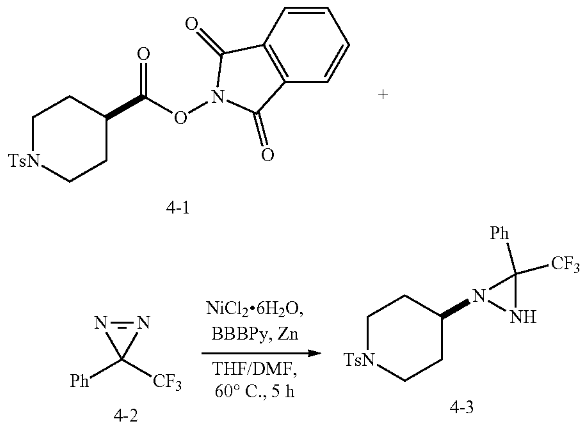

4-1

4-2

4-3

A culture tube fitted with rubber lined cap containing a magnetic stirbar was flame dried and then cooled under argon. To this vial the redox-active ester 4-1 (43.0 mg, 0.1 mmol, 1 eq.) and Zn (3.30 mg, 0.05 mmol, 0.5 eq.) were added, and vial was back flushed with argon three times. To this, 0.3 mL dry THF was added. In another flame-dried reaction vial $NiCl_2.6H_2O$ (4.8 mg, 0.02 mmol, 0.2 eq.) and 4,4'-Bis(1,1-dimethylethyl)-2,2'-bipyridine (11.0 mg, 0.04 mmol, 0.4 eq.) were added. The catalyst was dissolved in 0.2 mL dry DMF and stirred for 10 minutes during which the solution becomes teal blue. To the reaction mixture containing redox-active ester, the catalyst solution was added followed immediately the diazirine 4-2 (28.0 mg, 0.15 mmol, 1.5 eq.) The reaction mixture was stirred on pre-heated stirplate at 60° C. for 14 h. The reaction was quenched using sat. $NH_4C_1$ (approx. 5 mL) and brine (approx. 10 mL). This was extracted with ethyl acetate (3×15 mL). The combined organic fractions were dried over $MgSO_4$, filtered and concentrated under reduced pressure. The crude product was purified by column chromatography on silica gel by gradient elution of 0-20% ethyl acetate in hexanes. This yielded the pure product as a white solid (21.0 mg, 50%).

General Procedure: Iron-Catalyzed One Pot Synthesis of Substituted Diaziridines

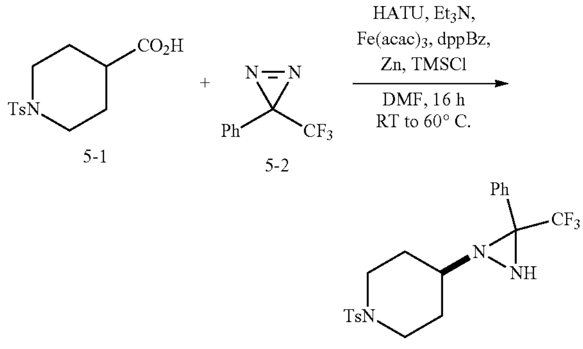

5-1

5-2

5-3

A culture tube lined with rubber cap containing a magnetic stirbar was flame-dried and then cooled under argon. The acid 5-1 (30.1 mg, 0.1 mmol, 1 eq.) and HATU (40.4 mg, 0.1 mmol, 1 eq.) were added. The vial was back flushed with argon three times. To the reaction vial 100 μL of DMF, 14 μL of triethylamine (10.1 mg, 0.1 mmol, 1 eq.) was added and stirred at room temperature for 2 h under argon atmosphere. By this time the reaction mixture became clear. In another flame-dried vial, $Fe(acac)_3$ (7.1 mg, 0.02 mmol, 20 mol %, 0.2 eq.) and dppBz ligand (11.2 mg, 0.025 mmol, 25 mol %, 0.25 eq.) were dissolved in 200 μL DMF and stirred for 10 min. to homogeneity. To the acid solution Zn (20.8 mg, 0.3 mmol, 3 eq.) and 38 μL TMSCl (32.6 mg, 0.3 mmol, 3 eq.) were added. The catalyst solution was then added, followed immediately by diazirine 5-2 (28.0 g, 0.15 mmol, 1.5 eq.). The reaction vial was then put in a preheated metal block at 60° C. covered with aluminum foil for 14 h. The reaction was quenched using sat. $NH_4Cl$ and brine and then extracted with ethyl acetate (3×15 mL). The combined organic fractions were dried over $MgSO_4$, filtered and concentrated under reduced pressure. The crude product was purified by column chromatography with silica gel. This yielded pure product, compound 5-3, as a white solid (26.3 mg, 58%).

General Procedure: Amination Using HCl and $I_2$

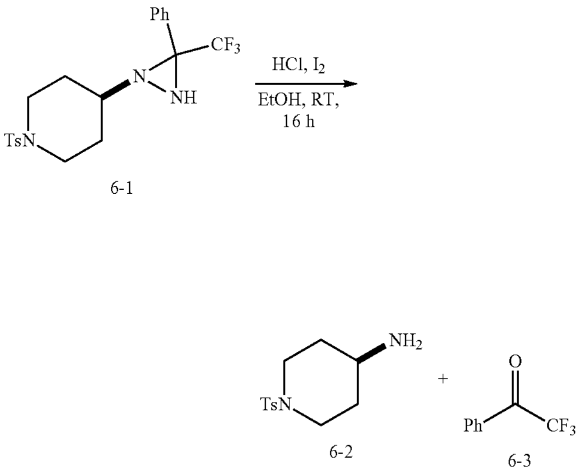

6-1

6-2

6-3

N-tosylpiperidine diaziridine 6-1 (23.3 mg, 0.05 mmol, 1 eq.) was dissolved in ethanol (0.1 M). To this solution conc. HCl was added to adjust to pH to 2, followed by iodine (0.0029 g, 0.1 mmol, 2 eq.). When TLC confirmed the disappearance of the starting material the reaction was quenched by addition of sat. $Na_2S_2O_3$ (till the color disappears) and 0.5 mL of 1 M NaOH. The reaction mixture was stirred for 2 h and extracted using DCM (2×10 mL). The combined organic fractions were dried using $MgSO_4$, filtered and concentrated under reduced pressure. The residue obtained was washed with hexanes to remove the byproducts and impurities. The white solid obtained after the hexanes wash was 1-tosylpiperidin-4-amine 6-2 (0.0100 g, 72%).

General Procedure: Amination Using HCl and NaI

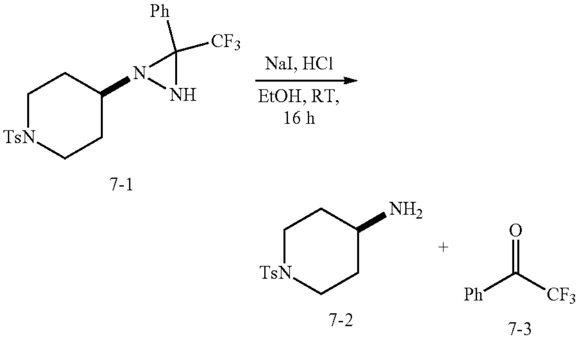

7-1

7-2

7-3

The N-tosylpiperidine diaziridine 7-1 (0.0239 g, 0.05 mmol, 1 eq.) was dissolved in ethanol (0.05 M). To this solution conc. HCl was added to adjust pH to 2, followed by NaI (0.0075 g, 0.1 mmol, 2 eq.). When TLC confirmed the disappearance of the starting material the reaction was quenched by addition of sat. $Na_2S_2O_3$ (till the color disappears) and 0.5 mL of 1 M NaOH. The reaction mixture was stirred for 2 h and extracted using DCM (2×10 mL). The combined organic fractions were dried using $MgSO_4$, filtered and concentrated under reduced pressure. The residue obtained was washed with hexanes to remove the byproducts and impurities. The white solid obtained after the hexanes wash was 1-tosylpiperidin-4-amine 7-2 (0.0110 g, 77%).

General Procedure: Amination Using TMSCl and LiCl

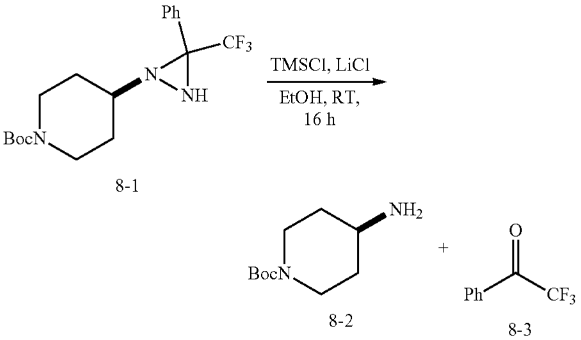

8-1

8-2

8-3

N-bocpiperidine diaziridine 8-1 (37.2 mg, 0.1 mmol, 1 eq.) was dissolved in DMF (0.3 M). To this solution TMSCl (0.0326 g, 38 μL, 0.3 mmol, 3 eq.) and LiCl (12.7 mg, 0.3 mmol, 3 eq.) were added. The reaction was stirred at 60° C. for 12 h until the TLC confirmed the disappearance of the starting material. To this reaction mixture 200 μL of deionized (DI) $H_2O$ was added and stirred for 3 h at 60° C. followed by addition of 200 μL of 1 M NaOH (pH adjusted to 12) continued stirring for 30 min at 60° C. The solution was then cooled and the reaction mixture was diluted with 10 mL $H_2O$. The solution was then extracted with ethyl acetate (2×10 mL). The combined organic fractions were washed with (4×10 mL) brine to remove residual DMF, dried using $MgSO_4$, filtered and concentrated under reduced pressure. The residue was purified by column chromatography on silica gel using gradient elution 0-10% MeOH in DCM (with 1% $NH_4OH$) to obtain t-butyl-4-aminopiperidine-1-carboxylate 8-2 (0.0180 g, 90%). The characterization data matched with the values in the literature.

General Procedure: One Pot Amination

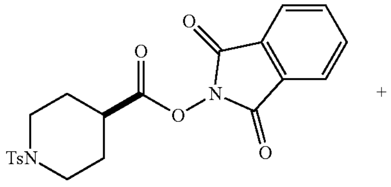

9-1

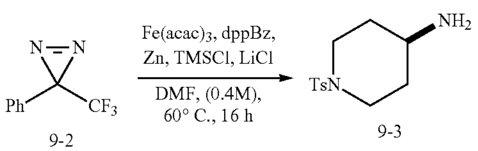

9-2 9-3

A culture tube fitted with rubber lined cap with a magnetic stirbar was flame-dried and cooled under an argon balloon. The redox-active ester 9-1 (43 mg, 0.1 mmol, 1 eq.), Zn (20 mg, 0.3 mmol, 3 eq.) and LiCl (13 mg, 0.3 mmol, 3 eq.) were added to the vial followed by back flushing with argon. In another small flame-dried reaction vial, $Fe(acac)_3$ (7.1 mg, 0.02 mmol, 20 mol %, 0.2 eq.) and dppBz ligand (11.2 mg, 0.025 mmol, 25 mol %, 0.25 eq.) were added under argon atmosphere. This catalyst system was dissolved in 0.3 mL dry DMF. After stirring for 10 minutes a homogeneous mixture was formed. To the dry reaction mixture of the RAE and Zn, TMSCl (38 μL, 0.3 mmol, 3 eq.) was added. This was followed by addition of catalyst using a syringe, followed immediately by addition of the diazirine 9-2 (0.028 g, 0.15 mmol, 1.5 eq.). After addition of all the reagents was complete, the vial was covered with aluminum foil and kept stirring on the preheated stirplate at 60° C. The reaction was heated overnight. The reaction mixture was recharged with LiCl (13 mg, 0.3 mmol, 3 eq.) and TMSCl (38 μL, 0.3 mmol, 3 eq.) and continued stirring for another 3 hours. To this reaction mixture 200 μL of deionized (DI) $H_2O$ was added and stirred for 3 h at 60° C. followed by addition of 200 μL of 1 M NaOH (pH adjusted to 12) continued stirring for 30 min at 60° C. The solution was then cooled and the reaction mixture was diluted with 10 mL $H_2O$. The solution was then extracted with ethyl acetate (2×10 mL). The combined organic fractions were washed with (4×10 mL) brine to remove residual DMF, dried using $MgSO_4$, filtered and concentrated under reduced pressure. The residue was purified by column chromatography on silica gel using gradient elution 0-10% MeOH in DCM (with 1% $NH_4OH$) to obtain compound 9-3 (0.0162 g, 63%).

General Procedure: Synthesis of Hydrazines

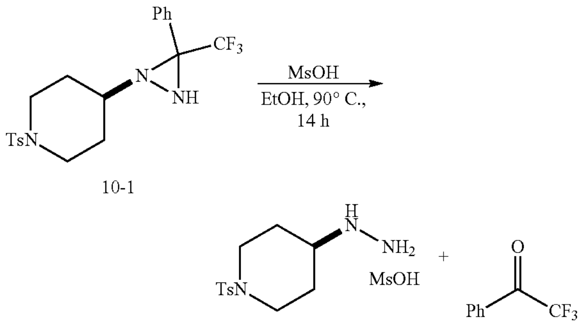

10-1

10-2 10-3

N-tosylpiperidine diaziridine 10-1 (0.0419 g, 0.1 mmol, 1 eq.) was suspended in ethanol (0.1 M). To this methane sulfonic acid (MsOH) (38 μL, 0.6 mmol, 6 eq.) was added and stirred at 90° C. for 14 h. The reaction mixture was then concentrated under reduced pressure. The crude $^1$H NMR showed almost quantitative yield ( ). The isolated compound was obtained by precipitation using diethyl ether or n-pentane. The white solid obtained was washed with acetone and dried on high vac to get pure compound 10-2 (0.0198 g, 55%). The compound was unstable to high heat; decomposed on under high heat and vacuum or if stored at room temperature for a long time.

General Procedure for Fluorous Solid Phase Extraction (F-SPE)

1) Obtained a new cartridge and fitted it on the F-SPE chamber. Washed the new cartridge with 1 mL of DMF (this can be skipped with recycled cartridges) followed by 80% MeOH in water. Discarded the eluent.
2) Dissolved the crude sample in 0.5 mL DMF and loaded it on the cartridge. Washed with 80% MeOH in water solution (10 mL) and collected the eluent as non-fluorous phase. Removed the volatiles under reduced pressure. Extracted the product using ethyl acetate from the aqueous phase. Concentrated the organic layers, dried it over $MgSO_4$, and concentrated under reduced pressure.
3) Washed the cartridge with MeOH (10 mL) to collect the eluent for fluorous phase fraction. Dried the fraction over $MgSO_4$ to remove remnant water from previous step. Evaporated MeOH under reduced pressure.
4) To regenerate the cartridge, it was washed with 10-12 mL THF. Dried the cartridge in a chamber under vacuum.

General Procedure: Synthesis of Substituted Diaziridines Using F-SPE

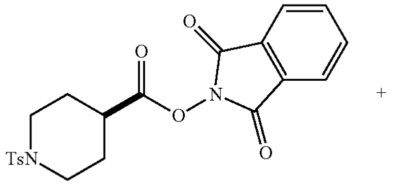

11-1

-continued

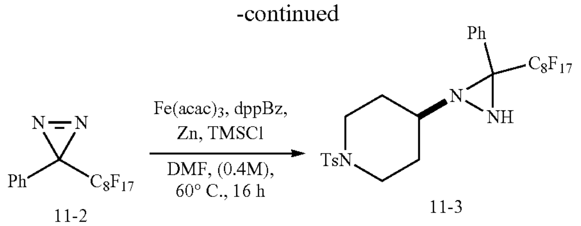

11-2

11-3

A culture tube fitted with rubber lined cap with a magnetic stir bar was flame-dried and cooled under an argon balloon. The redox-active ester 11-1 (43 mg, 0.1 mmol, 1 eq.) and Zn (20 mg, 0.3 mmol, 3 eq.) were added to the vial followed by back flushing with argon. In another small flame-dried reaction vial, $Fe(acac)_3$ (7.1 mg, 0.02 mmol, 20 mol %, 0.2 eq.) and dppBz ligand (11.2 mg, 0.025 mmol, 25 mol %, 0.25 eq.) were added under argon atmosphere. This catalyst system was dissolved in 0.3 mL dry DMF. After stirring for 10 minutes a homogeneous mixture was formed. To the dry reaction mixture of the RAE and Zn, TMSCl (38 μL, 0.3 mmol, 3 eq.) was added. This was followed by addition of catalyst using a syringe, followed immediately by addition of the diazirine 11-2 (0.028 g, 0.15 mmol, 1.5 eq.). After addition of all the reagents was complete, the vial was covered with aluminum foil and kept stirring on the pre-heated stirplate at 60° C. The reaction was heated overnight. After complete consumption of the RAE confirmed by TLC, the reaction was quenched with sat. $NH_4Cl$ (approx. 10 mL) and brine (30 mL). The solution was extracted using ethyl acetate (3×20 mL). The combined organic fractions were dried with $MgSO_4$, filtered and then concentrated under reduced pressure. The general procedure for F-SPE was followed to get rid of byproducts and impurities whereas the fluorous phase contained 11-3 and excess diazirine 11-2 from the reaction. The concentrated fluorous fraction was washed with hexanes to recover diazirine 11-2. The white solid obtained after hexanes wash was pure 11-3 (68 mg, 88%).

Publications cited herein are hereby specifically incorporated by reference in their entireties and at least for the material for which they are cited.

While it should be understood that while the present disclosure has been provided in detail with respect to certain illustrative and specific aspects thereof, it should be considered limited to such, as numerous modifications are possible without departing from the broad spirit and scope of the present disclosure as defined in the appended claims. It is, therefore, intended that the appended claims cover all such equivalent variations as fall within the true spirit and scope of the invention.

What is claimed is:

1. A compound of the formula

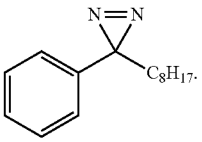

* * * * *